United States Patent [19]

Monkovic et al.

[11] Patent Number: 4,808,624
[45] Date of Patent: Feb. 28, 1989

[54] PHARMACOLOGICALLY ACTIVE SUBSTITUTED BENZAMIDES

[75] Inventors: Ivo Monkovic, Fayetteville; David Willner, Dewitt, both of N.Y.

[73] Assignee: Bristol-Myers Company, New York, N.Y.

[21] Appl. No.: 729,513

[22] Filed: May 6, 1985

Related U.S. Application Data

[63] Continuation-in-part of Ser. No. 625,742, Jun. 28, 1984, abandoned.

[51] Int. Cl.$^4$ ............... A61K 31/275; A61K 31/165; C07F 121/52; C07F 103/22
[52] U.S. Cl. .................................. 514/523; 558/389; 564/162; 564/164; 514/618; 514/619
[58] Field of Search ............... 558/389; 564/162, 164; 514/523, 618, 619

[56] References Cited

U.S. PATENT DOCUMENTS

| | | | |
|---|---|---|---|
| 3,177,252 | 4/1965 | Thomin et al. | 564/162 |
| 3,219,528 | 11/1965 | Thomin et al. | 564/162 |
| 3,357,978 | 12/1967 | Thomin et al. | 564/162 |

Primary Examiner—Anton H. Sutto
Attorney, Agent, or Firm—Richard P. Ryan

[57] ABSTRACT

Novel substituted benzamides of the formula

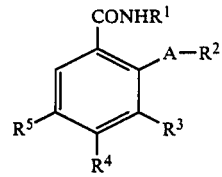

wherein $R^1$, $R^2$, $R^3$, $R^4$, $R^5$ and A are as defined herein are useful in the treatment of emesis, and particularly chemotherapy-induced emesis in cancer patients. Some of the compounds are also useful in disorders relating to impaired gastric motility.

9 Claims, No Drawings

PHARMACOLOGICALLY ACTIVE SUBSTITUTED BENZAMIDES

CROSS-REFERENCE TO RELATED APPLICATION

This application is a continuation-in-part of the copending application U.S. Ser. No. 625,742, filed June 28, 1984 and now abandoned.

SUMMARY OF THE INVENTION

This invention relates to novel substituted benzamides of the formula

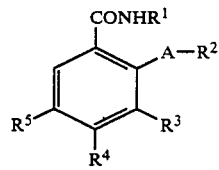

wherein $R^1$, $R^2$, $R^3$, $R^4$, $R^5$ and A are as defined below, which are useful in the treatment of emesis, particularly chemotherapy-induced emesis, such as cisplatin treatment of cancer patients, and/or in treatment of disorders related to impaired gastric motility, such as retarded gastric emptying, dyspepsia, flatulence, esophageal reflux and the like.

BACKGROUND AND PRIOR ART

Emesis is a common and serious problem in patients receiving cancer chemotherapeutic agents. In a significant number of patients, nausea and vomiting is so severe that they discontinue their course of chemotherapeutic treatment prior to its completion. Although no known antiemetic agent is totally effective in alleviating the emesis associated with chemotherapy, there are a large number of compounds (many based on the substituted benzamide structure) which have good antiemetic activity.

Although the complete mechanism of action of antiemetic agents is not known, the effective antiemetic agents are generally dopaminergic antagonists. Indeed, screening for potential antiemetic agents typically is conducted via tests designed to determine dopaminergic blockage, e.g. spiperone binding tests in vitro and apomorphine emesis tests in dogs. As a result of their dopaminergic antagonism and/or central nervous system depression, known antiemetic agents have undesirable side effects such as sedation, dystonic reactions, diarrhea and akathisia.

We have surprisingly found a group of substituted benzamide antiemetic agents with a high specificity of action, which are not dopaminergic antagonists and which are free of the undesirable side effects of the presently known antiemetic agents.

An excellent, modern review article on the variously substituted benzamides and their pharmacological activities is found in "Chemical Regulation of Biological Mechanisms", A. M. Creighton and S. Turner, editors, Royal Society of London (1982), in the chapter entitled "Substituted Benzamides as Dopamine Antagonists", by M. S. Hadley (Pages 140-153). It states that this class of compounds is defined by the formulae

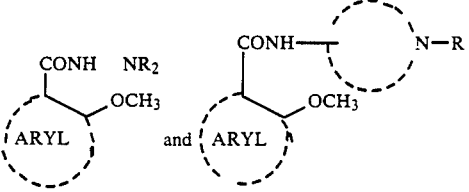

in which the aryl ring is most commonly the phenyl ring and where "a methoxy group ortho to the benzamide moiety is almost invariably present." It points out that the diverse actions of the substituted benzamides can be considered as being a consequence of the compounds being dopamine antagonists.

Representative prior art patents disclosing N-substituted benzamides, having various substituents on the phenyl ring, include the following.

U.S. Pat. No. 3,219,528, issued Nov. 23, 1965 to M. L. Thominet, discloses substituted benzamides of the formula

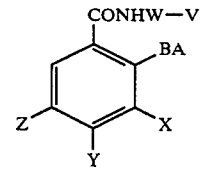

wherein V is

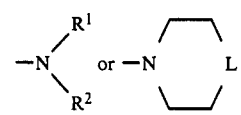

in which $R^1$ and $R^2$ are alkyl, L is oxygen, methylene or NR in which R is hydrogen, alkyl or alkylsulfamoyl; W is alkylene; A is alkyl; B is sulfur or oxygen; and X, Y and Z are hydrogen, halogen, alkoxy, nitro, amino, alkylamino, dialkylamino, (lower)acyl, (lower)acylamino, cyano, alkylmercapto, sulfamoyl, alkylsulfamoyl, dialkylsulfamoyl or halomethyl. The compounds are apomorphine antagonists and are stated to be antiemetic agents. U.S. Pat. Nos. 3,177,252, issued Apr. 6, 1965, and 3,312,739, issued Apr. 4, 1967, are related and have similar disclosures.

United Kingdom Pat. No. 1,500,105, published Feb. 8, 1978, discloses substituted benzamides of the formula

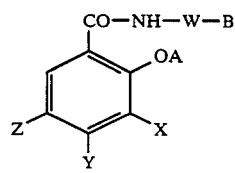

wherein A is hydrogen, $C_{1-5}$ alkyl or $C_{2-5}$ alkenyl; X is hydrogen, $C_{1-5}$ alkoxy, $C_{2-5}$ alkyl, $C_{2-5}$ alkenyloxy or $C_{2-5}$ alkenyl; Y is hydrogen, halogen, nitro, $C_{1-5}$ alkyl, $C_{1-5}$ alkoxy, amino or substituted amino; Z is hydrogen, halogen, $C_{1-5}$ alkoxy, $C_{1-5}$ alkylsulfonyl or a group of the formula $-SO_2NR^1R^2$ in which $R^1$ and $R^2$ are the same or different and are hydrogen or $C_{1-5}$ alkyl group, or $-NR^1R^2$ is a heterocyclic ring optionally containing another heteroatom; W is a $C_{1-5}$ straight or branched chain alkylene group; B is $-NR^3R^4$ in which $R^3$ is $C_{1-5}$ alkyl and $R^4$ is $C_{1-5}$ hydroxyalkyl, or B is a nitrogen-attached heterocyclic ring optionally containing a second nitrogen atom and optionally having a substituent, or B is a racemic, dextrorotatory or levorotatory heterocyclic ring of the formula

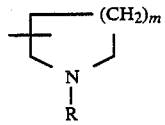

in which R is $C_{1-5}$ alkyl containing a reactive function such as hydroxy, mercapto, oxo, thioxo, oxa or thia; and m is 1, 2 or 3; and acid addition salts, oxides and quaternary ammonium salts thereof. The compounds are stated to be apomorphine antagonists and to have valuable therapeutic properties, particularly as antiemetics.

U.S. Pat. No. 4,207,327, issued June 10, 1980 to C. D. Lunsford et al., discloses compounds of the formula

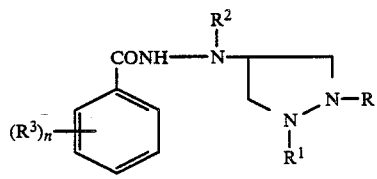

wherein R is alkyl, cycloalkyl or phenylalkyl; $R^1$ is alkyl, cycloalkyl or phenylalkyl; $R^2$ is hydrogen, alkyl or phenyl; and $R^3$ is hydroxy, cyano, nitro, amino, fluoro, chloro, bromo, trifluoromethyl, alkyl, alkoxy, sulfamoyl or acetamido, and each $R^3$ may be the same or different. The compounds are stated to have antiemetic and gastric emptying properties.

U.S. Pat. No. 3,966,957, issued June 29, 1976 to Cale, Jr., et al., discloses substituted benzamides of the formula

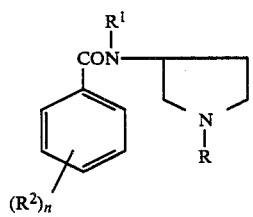

wherein R is cycloalkyl, phenyl or phenylalkyl; $R^1$ is hydrogen, $C_{1-8}$ alkyl or phenyl; $R^2$ is halogen, alkyl, alkoxy, amino, nitro, alkylamino, dialkylamino, mercaptomethyl, acetamido, sulfamoyl, cyano, hydroxy, benzyloxy or trifluoromethyl; and n is 0–3; and substituted thiobenzamides of the formula

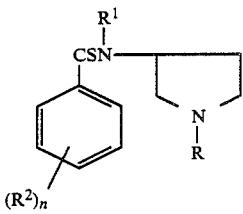

wherein R is cycloalkyl; $R^1$ is hydrogen, or $C_{1-8}$ alkyl; $R^2$ is nitro, amino, halogen, sulfamoyl or alkoxy; and n is 0–3; and pharmaceutically acceptable acid addition salts thereof. U.S. Pat. No. 3,963,745 is related and has a substantially identical disclosure. The compounds are stated to be apomorphine antagonists and to be useful as antiemetics. Certain of the compounds were stated to reduce catalepsy in rats.

COMPLETE DISCLOSURE

This invention relates to compounds of the formula

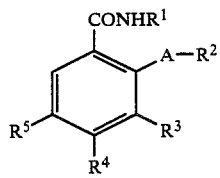

wherein
$R^3$ is hydrogen or, when $R^4$ and $R^5$ are each hydrogen, $R^3$ may be (lower)alkoxy;
$R^4$ is hydrogen, amino or (lower)alkoxy;
$R^5$ is hydrogen, chloro, bromo, fluoro, trifluoromethyl, (lower)alkylthio, (lower)alkanesulfinyl, (lower)alkanesulfonyl, sulfamyl or

or $R^4$ and $R^5$, taken together, may be $-HN-N=N-$;
$R^6$ is (lower)alkyl, (lower)alkenyl or (lower)alkynyl;
$R^1$ is

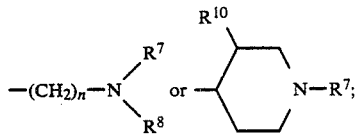

n is an integer of from 1 to 4, inclusive;
$R^7$ and $R^8$ are teh same or different and are (lower)alkyl, (lower)alklenyl, (lower) alkynyl,

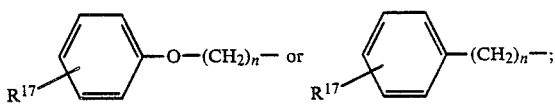

$R^{10}$ is hydrogen or (lower) allkoxy;
$R^{17}$ is hydrogen, halogen, hydroxy, (lower)alkyl or (lower)alkoxy;
A is oxygen or $$-\overset{(O)_p}{\underset{|}{S}}-;$$

$R^2$ is $$-\underset{|}{\overset{R^{12}}{C}}HOCH_2CH_2OR^{11}, \quad -\underset{|}{\overset{R^{12}}{C}}HCH_2OR^{11}, \quad -\underset{\underset{R^{13}}{|}}{\overset{R^{12}}{\underset{|}{C}}}-\overset{X}{\underset{R^{14}}{\overset{\|}{C}}},$$

$$-\underset{\underset{R^{13}}{|}}{\overset{R^{12}}{\underset{|}{C}}}-\underset{OR^{15}}{\overset{R^{14}}{\underset{|}{C}}}-R^9, \quad -\underset{\underset{R^{13}}{|}}{\overset{R^{12}}{\underset{|}{C}}}-\overset{O}{\underset{O}{\overset{|}{C}H}}(CH_2)_m, \quad -\overset{R^{12}}{\underset{|}{C}H}(CH_2)_qB,$$

$$-\underset{\underset{R^{13}}{|}}{\overset{R^{12}}{\underset{|}{C}}}-CN, \quad -N\underbrace{\phantom{XXX}}Z, \quad -CH_2\underset{R^{19}}{\overset{O-N}{\diagdown\hspace{-2pt}\diagup}}R^{18} \text{ or}$$

$$-\underset{\underset{R^{13}}{|}}{\overset{R^{12}}{\underset{|}{C}}}-\underset{\underset{OR^{21}}{|}}{CH}-\underset{\underset{OR^{20}}{|}}{CH}-R^{14};$$

X is oxygen, sulfur or =NOR$^{16}$;
Z is —(CH$_2$)$_p$—, O, N or $$-\overset{(O)_p}{\underset{|}{S}}-;$$

B is $$-NH\overset{O}{\overset{\|}{C}}R^9, \quad -\overset{(O)_p}{\underset{|}{S}}-R^9, \quad -N\overset{R^9}{\underset{R^9}{\diagdown\hspace{-2pt}\diagup}}, \quad -\overset{O}{\overset{\|}{C}}-N\overset{R^9}{\underset{R^9}{\diagdown\hspace{-2pt}\diagup}}, \quad -C\underset{\underset{H}{N}}{\overset{N}{\diagup\hspace{-2pt}\diagdown}}(CH_2)_r$$

pyridyl or oxazolidinyl;
m is 2 or 3;
p is 0, 1 or 2;
q is an integer of from 0 to 4, inclusive;
r is 2 or 3;
$R^9$ is hydrogen or (lower)alkyl;
$R^{11}$, $R^{12}$, $R^{13}$, $R^{15}$ and $R^{16}$ are the same or different, and are hydrogen, (lower)alkyl, (lower)alkenyl, (lower)alkynyl, (lower)alkoxy(lower)alkyl, cycloalkyl containing from 5 to 7 carbon atoms, inclusive, or

[benzyl group with $R^{17}$ substituent]—(CH$_2$)$_n$—, provided that, when $R^{11}$, $R^{15}$ or $R^{16}$ is (lower)alkenyl or (lower)alkynyl, the unsaturated carbon atom may not be directly attached to an oxygen or nitrogen atom;
$R^{14}$ is hydrogen, halogen, (lower)alkyl, (lower)alkenyl, (lower)alkynyl, cycloalkyl containing from 5 to 7 carbon atoms, inclusive, hydroxy, (lower)alkoxy, (lower)alkenyloxy, (lower)alkoxycarbonyl(lower)alkenyl, hydrazino, acetylhydrazino, thienyl, phenyl, $$\overset{R^{11}}{\underset{R^{12}}{\diagdown}}N- \quad \text{or} \quad [\text{phenyl ring with } R^{17}]-(CH_2)_n-;$$

$R^{18}$ and $R^{19}$ are the same or different and are hydrogen or (lower)alkyl;
$R^{20}$ and $R^{21}$ are each hydrogen or, taken together, represent $$\overset{\diagdown}{\underset{H_3C}{\diagup}}\overset{\diagup}{\underset{CH_3}{\diagdown}}C \quad \text{or} \quad \overset{\diagdown}{\underset{H_3C}{\diagup}}CH_2-\overset{\diagup}{\underset{CH_3}{\diagdown}}C \quad;$$

or $R^{12}$ and $R^{13}$, taken together with the carbon atom to which they are attached, may form a saturated ring of from 5 to 7 atoms, inclusive, optionally containing at least one heteroatom selected from oxygen, sulfur and nitrogen;
or $R^{12}$ and $R^{14}$, taken together with the carbon atoms to which they are attached, may form a saturated or unsaturated ring of from 5 to 7 atoms, inclusive, optionally containing at least one heteroatom selected from oxygen, sulfur and nitrogen;
or $R^{14}$ and $R^{15}$, taken together with the carbon and oxygen atoms to which they are attached, may form a 3 to 7 membered saturated oxygen-containing ring;
or nontoxic pharmaceutically acceptable salts, hydrates, solvates or quaternary ammonium salts thereof.

A more preferred group of the compounds of Formula I are those of the formula

[benzene ring structure with CONHR$^1$, O—R$^2$, R$^3$, Cl, NH$_2$ substituents]   I wherein
$R^3$ is hydrogen or, when $R^4$ and $R^5$ are each hydrogen, $R^3$ may be (lower)alkoxy;
$R^1$ is $$-(CH_2)_n-N\overset{R^7}{\underset{R^8}{\diagdown\hspace{-2pt}\diagup}} \quad \text{or} \quad [\text{piperidine ring with } R^{10}]-N-R^7;$$

n is an integer of from 1 to 4, inclusive;
$R^7$ and $R^8$ are the same or different and are (lower)alkyl, (lower)alkenyl or (lower)alkynyl;
$R^{10}$ is hydrogen or (lower)alkoxy;
$R^2$ is

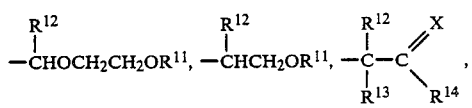, 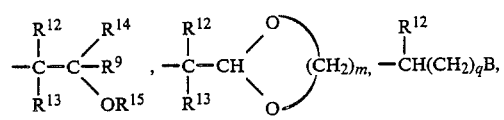

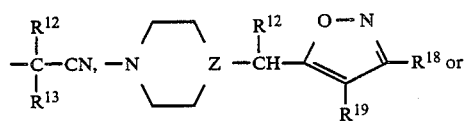

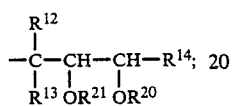;

X is oxygen, sulfur or =NOR$^{16}$;
Z is —(CH$_2$)$_p$—, O, N or

;

B is

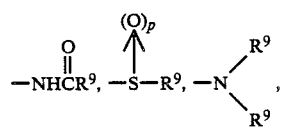,

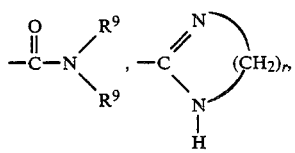

pyridyl or oxazolidinyl;
m is 2 or 3;
p is 0, 1 or 2;
q is an integer of from 0 to 4;
r is 2 or 3;
R$^9$ is hydrogen or (lower)alkyl;
R$^{11}$, R$^{12}$, R$^{13}$, R$^{15}$ and R$^{16}$ are the same or different, and are hydrogen, (lower)alkyl, (lower)alkenyl, (lower)alkynyl, (lower)alkoxy(lower)alkyl or cycloalkyl containing from 5 to 7 carbon atoms, inclusive, provided that, when R$^{11}$, R$^{15}$ or R$^{16}$ is (lower)alkenyl or (lower)alkynyl, the unsaturated carbon atom may not be directly attached to an oxygen or nitrogen atom;
R$^{14}$ is hydrogen, halogen, (lower)alkyl, (lower)alkenyl, (lower)alkynyl, cycloalkyl containing from 5 to 7 carbon atoms, inclusive, (lower)alkoxy, hydroxy, (lower)alkenyloxy, hydrazino, (lower)alkoxycarbonyl(lower)alkyl, acetylhydrazino, thienyl, phenyl, phenyl(lower)alkyl or

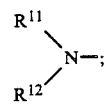

R$^{18}$ and R$^{19}$ are the same or different and are hydrogen or (lower)alkyl;
R$^{20}$ and R$^{19}$ are each hydrogen or, taken together, represent

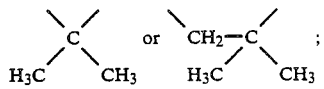;

or R$^{12}$ and R$^{14}$, taken together with the carbon atoms to which they are attached, may form a saturated or unsaturated ring of from 5 to 7 atoms, inclusive, optionally containing at least one heteroatom selected from oxygen, sulfur and nitrogen;
or R$^{14}$ and R$^{15}$, taken together with the carbon and oxygen atoms to which they are attached, may form a 3 to 7 membered saturated oxygen-containing ring;
or nontoxic pharmaceutically acceptable salts, hydrates, solvates or quaternary ammonium salts thereof.

A still more preferred group of the compounds of Formula I are those of the formula

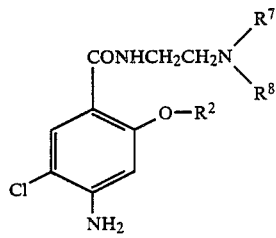

I wherein
R$^7$ and R$^8$ are the same or different and are ethyl or methyl;
R$^2$ is

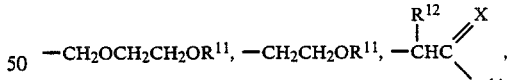

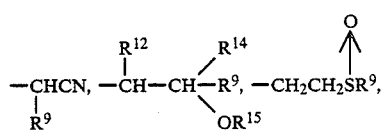

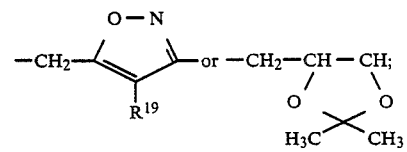

X is oxygen or =NOR$^{16}$;
R$^9$ is hydrogen or (lower)alkyl;
R$^{11}$, R$^{12}$, R$^{15}$ and are the same or different, and are hydrogen, (lower)alkyl, (lower)alkenyl, (lower- )alkynyl (lower)alkoxy(lower)alkyl or cycloalkyl containing from 5 to 7 carbon atoms, inclusive, provided that, when $R^{11}$, $R^{15}$ or $R^{16}$ is (lower)alkenyl or (lower)alkynyl, the unsaturated carbon atom may not be directly attached to an oxygen or nitrogen atom;

$R^{14}$ is hydrogen, halogen, (lower)alkyl, (lower)alkoxy, hydroxy, hydrazino, (lower)alkoxycarbonyl(lower)alkenyl, acetylhydrazino, thienyl, phenyl, phenyl(lower)alkyl or

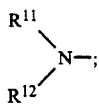

$R^{18}$ and $R^{19}$ are the same or different and are hydrogen or methyl;

or $R^{12}$ and $R^{14}$, taken together with the carbon atoms to which they are attached, may form a saturated or unsaturated ring of from 5 to 7 atoms, inclusive, optionally containing at least one heteroatom selected from oxygen, sulfur and nitrogen;

or $R^{14}$ and $R^{15}$, taken together with the carbon and oxygen atoms to which they are attached, may form a 3 to 6 membered saturated oxygen-containing ring;

or nontoxic pharmaceutically acceptable salts, hydrates, solvates or quaternary ammonium salts thereof.

Particularly preferred compounds of Formula I are 4-amino-5-chloro-N-[2-(diethylamino)ethyl]-2-(2-methoxyethoxy)benzamide,
4-amino-5-chloro-N-[2-(diethylamino)ethyl]-2-(2-hydroxyethoxy)benzamide,
4-amino-5-chloro-N-[2-(diethylamino)ethyl]-2-(2,2-dimethoxyethoxy)benzamide,
4-amino-5-chloro-N-[2-(diethylamino)ethyl]-2-[(2-methoxyethoxy)methyloxy]benzamide,
4-amino-5-chloro-N-[2-(diethylamino)ethyl]-2-(2-propanon-1-yl)oxybenzamide,
4-amino-2-benzoylmethyloxy-5-chloro-N-[2-(diethylamino)ethyl]benzamide,
4-amino-2-(butan-2-on-3-yl)oxy-5-chloro-N-[2-(diethylamino)ethyl]benzamide,
4-amino-5-chloro-2-(cyclohexanon-2-yl)oxy-N-[2-(diethylamino)ethyl]benzamide,
4-amino-5-chloro-N-[2-(diethylamino)ethyl]-2-(5-hexen-2-on-3-yl)oxybenzamide,
4-amino-5-chloro-N-[2-(diethylamino)ethyl]-2-[(2-hydroxyimino)propan-1-yl]oxybenzamide,
4-amino-5-chloro-N-[2-(diethylamino)ethyl]-2-[(2-methoxyimino)propan-1-yl]oxybenzamide,
4-amino-5-chloro-N-[2-(diethylamino)ethyl]-2-(2-hydroxypropan-1-yl)oxybenzamide,
4-amino-5-chloro-2-cyanomethyloxy-N-[2-(diethylamino)ethyl]benzamide,
4-amino-2-(carboxamidomethyloxy)-5-chloro-N-[2-(diethylamino)ethyl]benzamide acetate,
4-amino-2-(2-butyn-1-yl)oxy-5-chloro-N-[2-(diethylamino)ethyl]benzamide,
4-amino-5-chloro-N-[2-(diethylamino)ethyl]-2-[2-(methylsulfinyl)ethoxy]benzamide,
4-amino-5-chloro-N-[2-(diethylamino)ethyl]-2-(pentan-2-on-3-yl)oxybenzamide,
4-amino-2-(2-butanon-1-yl)oxy-5-chloro-N-[2-(diethylamino)ethyl]benzamide,
4-amino-5-chloro-N-[2-(diethylamino)ethyl]-2-(pentan-2-on-1-yl)oxybenzamide,
4-amino-5-chloro-2-(pentan-3-on-2-yl)oxy-N-(2-diethylaminoethyl)benzamide,
4-amino-5-chloro-N-[2-(diethylamino)ethyl]-2-(2-hydrazino-2-oxoethoxy)benzamide,
4threo-4-amino-5-chloro-N-[2-(diethylamino)ethyl]-2-(2-hydroxybut-3-yl)oxybenzamide,
erythro-4-amino-5-chloro-N-[2-(diethylamino)ethyl]-2-(2-hydroxybut-3-yl)oxybenzamide,
4-amino-5-chloro-N-[2-(diethylamino)ethyl]-2-[2-(methylamino)-2-oxoethoxy]benzamide,
4-amino-5-chloro-N-[2-(diethylamino)ethyl]-2-(ethyl-3-methoxycroton-4-yl)oxybenzamide,
4-amino-5-chloro-N-[2-(diethylamino)ethyl]-2-(1,3-dioxolan-2-yl)oxybenzamide,
4-amino-5-chloro-N-[2-(diethylamino)ethyl]-2-(oxazolidin)-2-one-5-ylmethyl)oxybenzamide,
4-amino-5-chloro-N-[2-(diethylamino)ethyl]-2-(2-pyridinomethyl)oxybenzamide,
4-amino-5-chloro-N-[2-(diethylamino)ethyl]-2-tetrahydrofurfuryloxybenzamide and
4-amino-5-chloro-N-[2-(diethylamino)ethyl]-2-(2-methoxyethoxyethyl)oxybenzamide,
and nontoxic pharmaceutically acceptable salts, hydrates, solvates and quaternary ammonium salts thereof.

Also included within the scope of this invention are all possible optical and geometric isomers of the compounds of Formula I, and tautomeric forms thereof, where applicable. In another aspect, this invention relates to processes for the preparation of the compounds of Formula I and to antiemetic and/or gastrokinetic compositions containing at least one compound of Formula I as an active ingredient.

The compounds of Formula I may be prepared via several procedures. In the preferred process, shown in Reaction Scheme 1, below, a compound of Formula II is reacted with a compound of Formula $R^2$-L (where L is a conventional leaving group) in the presence of a base as an acid scavenger, to produce the compound of Formula I.

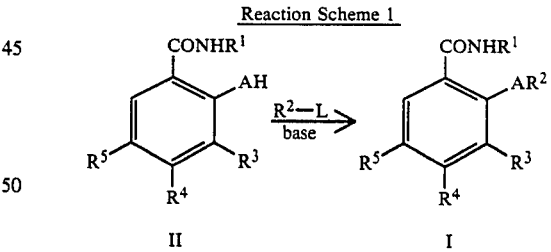

Reaction Scheme 1

Suitable leaving groups L are well-known to those skilled in the art and include, for example, chloro, bromo, iodo, methanesulfonyl, toluenesulfonyl and the like. The base may be a mild one such as $K_2CO_3$, $Na_2CO_3$ $MgSO_4$ or a quaternary ammonium hydroxide such as tetrabutylammonium hydroxide or benzyltriethylammonium hydroxide, or a mixture thereof. The reaction is conducted in an inert organic solvent such as acetone, acetonitrile, methylene chloride, dimethylformamide, dimethylacetamide, methanol, ethanol, isopropanol, diglyme, or the like. It is also possible to utilize sodium hydride or potassium hydride as the base, in an anhydrous, non-protonic organic solvent, or to use a strong base such as NaOH or KOH as a highly concentrated solution in a phase transfer solvent system such as $CH_2Cl_2/H_2O$, with the addition of a quaternary ammonium halide, sulfate or hydroxide as a phase transfer catalyst, e.g. tetrabutylammonium chloride, cetyltrimethylammonium bromide, benzyltriethylammonium chloride, or the like.

It will be apparent to those skilled in the art that Reaction Scheme 1 also may be varied to the extent that substituent groups $R^3$, $R^4$ and/or $R^5$ may be inserted into the compound of Formula I (or converted from a precursor group) as the final step, rather than being present in the compound of Formula II. Thus, for example, Compound I, where $R^5$ is hydrogen, may be chlorinated to produce Compound I in which $R^5$ is chloro. Similarly, $R^4$ of Compound I may be, for example, $-NO_2$, $-NHCOR$ or $-N=CHN(R)_2$ where R may be (lower)alkyl. The $-NO_2$ group may then be reduced to an amino group, or the $-NHCOR$ or $-N=CHN(R)_2$ groups may be hydrolyzed to an amino group.

We prefer to use an organic solvent-soluble tetrasubstituted ammonium salt as illustrated below for one of the preferred compounds of Formula I.

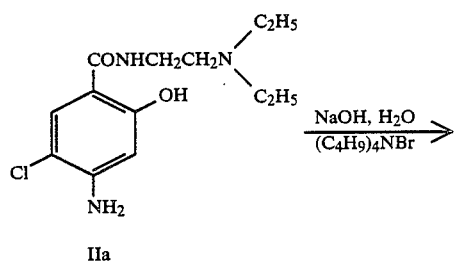

IIa

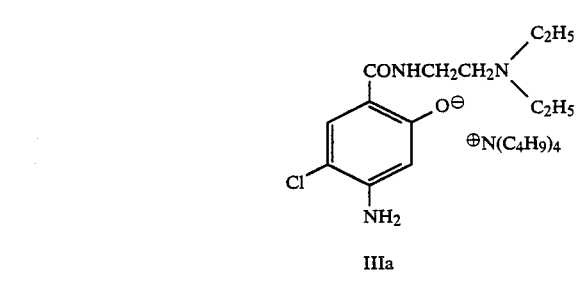

IIIa

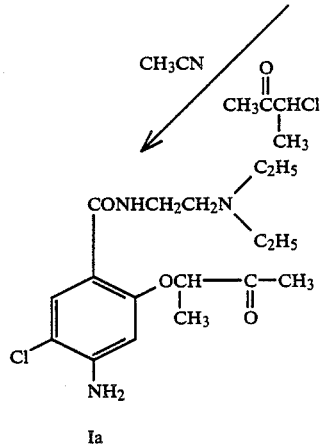

Ia

In the first step, Compound IIa is dissolved in aqueous sodium hydroxide and treated with one equivalent of tetrabutylammonium bromide. The quaternary ammonium salt IIIa precipitates from solution and is collected by filtration. It is then reacted with the desired alkylating agent in an inert organic solvent such as dimethylformamide, dimethylacetamide, actonitrile, tetrahydrofuran, $CHCl_3$, dimethylsulfoxide or diglyme, to produce the desired product Ia.

The intermeidate of Formula IIa may be prepared, for example, from demethylation of commercially available metoclopramide, having the formula metoclopramide Metoclopramide may be demethylated by methods well-known to those skilled in the art. Suitable procedures involve reaction with a thioalkoxide or thioaryloxide such as $NaSC_2H_5$, $KSC_2H_5$, $LiSC_2H_5$ or in an inert organic solvent such as dimethylformamide or dimethylsulfoxide, or by reaction with NaOH or KOH in a solvent such as ethylene glycol, propylene glycol or diglyme, or by reaction with 48% aqueous hydrobromic acid. We prefer to demethylate using $NaSC_2H_5$ in dimethylformamide.

It will be appreciated that certain 2-substituents may be difficult to insert directly into Compound IIa without elaborate protecting and deprotecting schemes. On the other hand, the initially inserted 2-substituent may be subsequently modified. Using Compound Ib, another preferred compound of this invention, as an example, various conversions are shown below Ib -continued

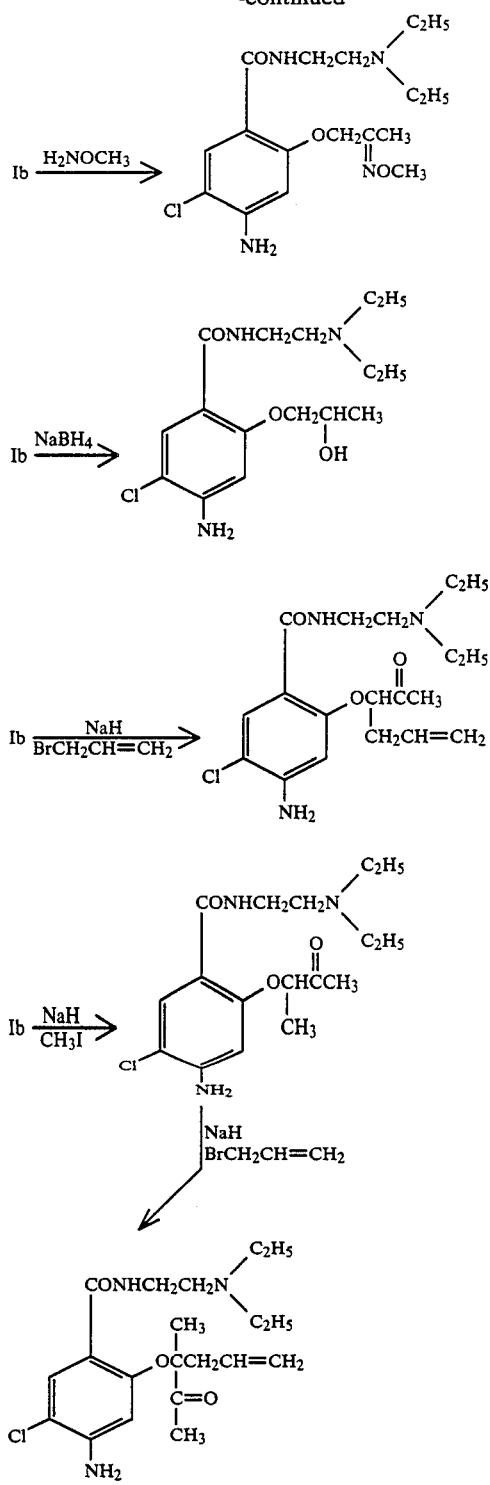

In an alternative procedure for the preparation of the compounds of Formula I, a compound of Forumula IV having the desired 2-substituent is reacted so as to introduce the desired aubstituted carboxamino group in the 1-position. As shown in Reaction Schemes 2a through 2h, there are several variants of this reaction procedure. A preferred 1-substitutent is shown for illustrative purposes.

Reaction Scheme 2

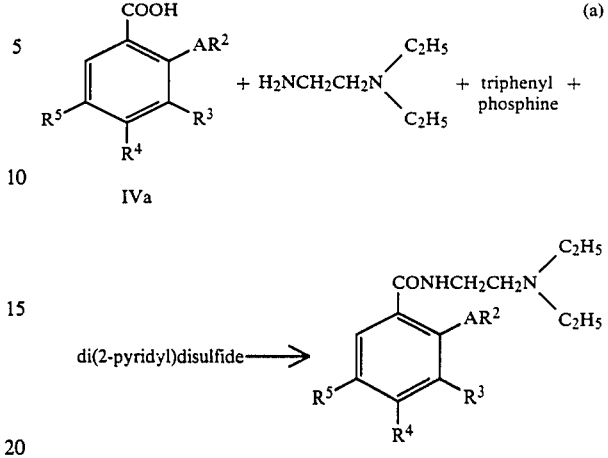
(a)

This reaction is described in greater detail, with the use of various disulfides and phosphorus compounds, in United Kingdom patent specification No. 1,449,524, published Sept. 15, 1976.

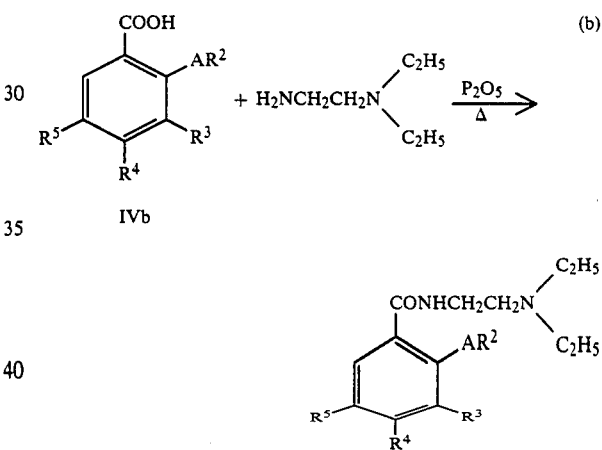
(b)

The starting material and the amine are heated to about 100° C, at which point the $P_2O_5$ is added and the temperature is raised to about 150° C. for a short period. This procedure is described in United Kingdom Patent Specification No. 1,441,352, published June 30, 1976.

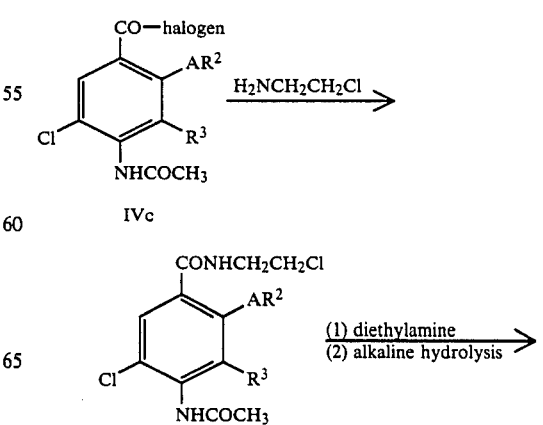
(c)

-continued

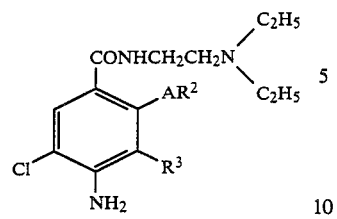

In this reaction, an amino substituent in the 4-position should be protected by acylation to a suitable amido group such as acetamido. Following the introduction of the 1-substituent, the 4-acetamido group is converted to an amino group by alkaline hydrolysis. This procedure, with variations, is described in United Kingdom Patent Specification No. 1,395,132, published May 21, 1975.

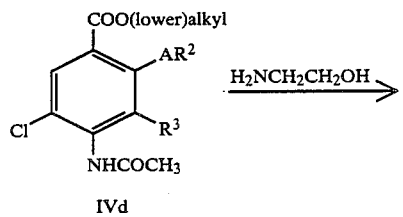

IVd

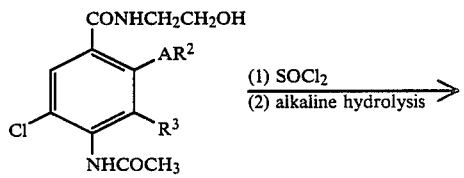

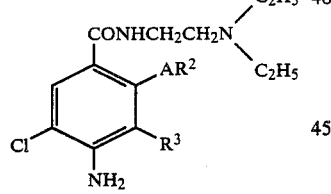

This reaction, a varaition of that shown in (d) above, is described in United Kingdom Patent Specification No. 1,395,131, published May 21, 1975.

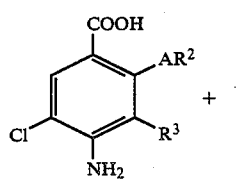

IVe

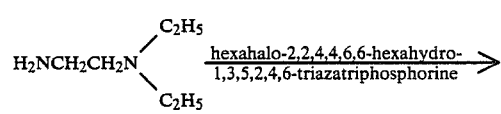

-continued

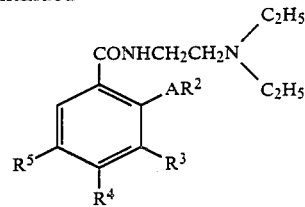

This procedure, and variations thereof, is described in United Kingdom Patent Specification No. 1,409,686, published Oct. 15, 1975.

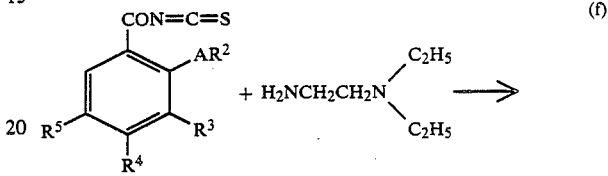 (f)

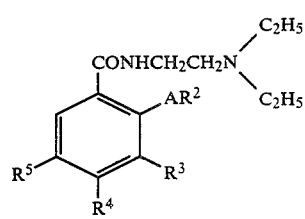

This procedure is described in published japanese Patent Applicaiton (Kokai) No. 51-026840, published Mar. 5, 1976.

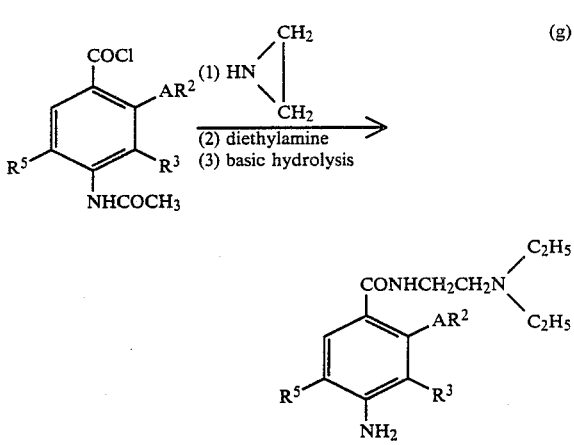 (g)

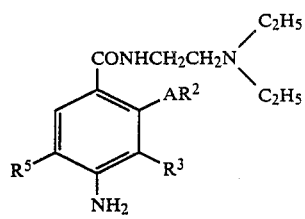

In this procedure, the 4-amino substituent is protected by acylation, e.g. formation of an acetamido group, which is subsequently hydrolyzed to the free amino group in the final product. This procedure, and variations thereof, is described in published Japanese Patent Appliication (Kokai) No. 47-18652, published Sept. 16, 1972.

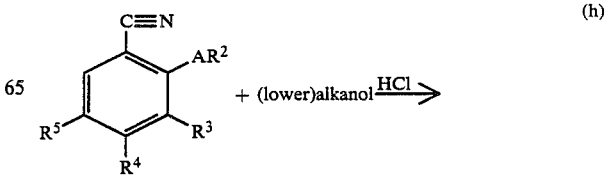 (h)

-continued

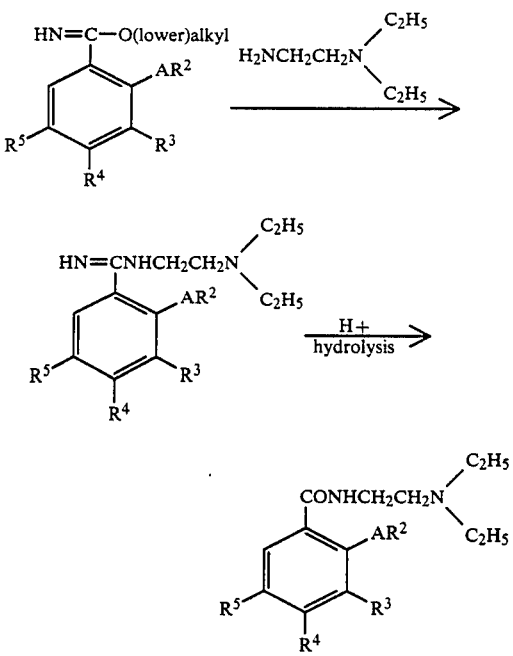

This procedure, and variations thereof, is described in Belgian Pat. No. 692,670, published July 17, 1967.

The physiology and neuropharmacology of emesis, and particularly chemotherapy-induced emesis, is not completely understood. The control mechanism for emesis consists of two distinct units in the medulla, the emetic center and the chemo-receptor trigger zone (CTZ). The emetic center, which is the final common pathway for all emetic stimuli, is located in the lateral reticular formation of the fourth ventricle. The CTZ is also located in the floor of the fourth ventricle, in the area postrema, and appears to be activated by chemical stimuli in the blood or cerebrospinal fluid. When stimulated, receptors, such as dopamine receptors, in the CTZ generate impulses which are transmitted to the emetic center, and emesis results. Reflex-induced vomiting may also be caused by irritation (and resulting stimuli) from the gastrointestinal tract or stimulation of receptors in the central nervous system. The cortex of the brain is believed to be another source of emesis. Thus, the familiar problem of anticipatory vomiting in patients receiving chemotherapy clearly is not associated with exogenous chemical stimulation. It is believed that anticipatory vomiting is mediated initially by the cortex which may then stimulate the medullary emetic center.

There are a number of commercially available antiemetic drugs at the present time, such as metoclopramide, bromopride, alizapride, clebopride, domperidone and nabilone. Metoclopramide is a leading compound and is utilized extensively in combination with cisplatin, which is an effective but highly emetogenic chemotherapeutic agent.

Presently available substituted benzamide antiemetic agents are generally dopaminergic antagonists and, indeed, are believed to exert their antiemetic activity by blocking dopamine receptors in the CTZ. Screening tests for potential antiemetic agents have historically involved tests which determine dopaminergic antagonist activity, e.g. spiperone binding tests in vitro, and the reduction of apomorphine-induced vomiting in the dog or cat.

The principal adverse effects of known substituted benzamide antiemetic agents are due to their dopamine blocking activity, and include akathisia, acute dystonia, Parkinsonian features and tardive dyskinesia, often along with nervous system depression.

The compounds of Formula I of the present invention are effective antiemetic agents but are not dopaminergic antagonists, as shown by both in vitro tests (spiperone binding) and in vivo tests (apomorphine emesis in the dog). Thus, the compounds of Formula I have good antiemetic activity (particularly against chemotherapy-induced emesis) with a high specificity of action, but with none of the side effect liabilities (such as described above) that are associated with the dopaminergic antagonist class of substituted benzamide antiemetic agents.

Many of the commercially available substituted benzamide antiemetic agents (such as metoclopramide) also have gastrokinetic activity and are useful in the treatment of disorders related to impaired gastrointestinal motility, such as retarded gastric emptying, dyspepsia, flatulence, esophageal reflux and the like. Some of the compounds of Formula I have been shown to have activity similar to metoclopramide in the field-stimulated guinea pig ileum test (Table 2), which is one standard screening test for gastrokinetic activity. Again, because they are not dopaminergic antagonists, the compounds of Formula I do not have the above-mentioned side-effect liabilities of the commercially available substituted benzamides such as metoclopramide or clebopride.

Biological Test Procedures (A) $^3$H-Spiperone Displacement

This test serves to detect compounds capable of displacing the radioactive spiperone ligand in vitro using striatal rat brain homogenates. It is used to identify compounds exhibiting an affinity to dopaminergic (D$_2$) receptors.

Rats (150±10 g; Charles River) were decapitated, the corpus striatum dissected out and frozen on dry ice. The tissues were pooled and stored at $-80°$ C. until used. Homogenates (Brinkmann Polytron) of the corpus striatum in cold HEPES.KOH buffer (final pH=7.4) were centrifuged at 39,000 x G. The supernatant was discarded and the pellets were re-suspended in HEPES.KOH buffer and re-centrifuged as above. The supernatant was again discarded and the pellets suspended in a buffer consisting of 50 mM HEPES.KOH containing 0.1% (w/v) ascorbic acid, 10 $\mu$M pargyline, 120 mM NaCl, 5 mM KCl, 2 mM CaCl$_2$ and 1 mM MgCl$_2$ at 20° C.; (final pH=7.4), at a concentration of 1 gm of wet tissue pellet per 100 ml of buffer mixture.

Tests to determine the Inhibitory Concentration$_{50}$ IC$_{50}$) of the compounds of Formula I and reference compounds versus $^3$H-spiperone were conducted as follows. Tubes containing either 100 $\mu$L of buffer mixture (for total binding), 100 $\mu$L of buffer mixture plus 100 $\mu$L of $10^{-4}$ M D(+)-butaclamol (for blanks, i.e. non-specific binding), or 100 $\mu$L of buffer mixture containing $10^{-7}$, $10^{-6}$ or $10^{-5}$ M test compound were prepared. To each were added 100 $\mu$L of a solution of $^3$H-spiperone (New England Nuclear) in buffer mixture (2000 c.p.m. in the incubation mixture) and 800 $\mu$L of the striatal tissue suspension. The tubes were then diluted to 1 mL with buffer mixture, giving a final concentration of $10^{-8}$, $10^{-7}$ M test compound and approximately 100 pM $^3$H-spiperone. The samples were incubated at 37° C. for 15 minutes, filtered in vacuo on glass fiber filters and counted by liquid scintillation spectrometry. For each of the test compounds, the $IC_{50}$ was not reached at the highest concentration ($10^{-6}$ $\mu$M = 1000 nM) of test compound, so the results in Table 2 were reported as >1000 nM. For the reference compounds, where the $IC_{50}$ was reached (or exceeded) with the original concentrations, the tests were repeated utilizing ¼, ½, 1, 2 and 4 times the concentration estimated (from the original concentrations) to be closest to the $IC_{50}$, so as to more accurately determine the $IC_{50}$. These latter results are reported in Table 2. All samples were run in duplicate.

(B) Antagonism of Apomorphine-Induced Emesis in Dogs

Unfasted beagle dogs of both sexes were used as test subjects. Test compounds and apomorphine were each administered subcutaneously as aqueous solutions, with the test compound being administered 30 minutes prior to the administration of the apomorphine. The dogs were observed for 60 minutes after administration of the apomorphine for either emesis or complete protection from emesis (quantal response).

Apomorphine was administered at a dose of 0.3 mg/kg. Since the test compounds were essentially void of apomorphine antagonism, they were administered at a dose of 3 mg/kg. Failure to reach 50% antagonism (prevention of emesis) at that dosage is reported in Table 1 as >3 mg/kg. Since the comparison compounds such as metoclopramide, alizapride, clebopride and domperidone have dopaminergic antagonist activity, lower doses of these standards were administered, and the calculated $ED_{50}$'s are reported in Table 1. All tests were run in at least two dogs.

(C) Antagonism of Cisplatin-Induced Emesis in the Ferret

Adult, male, castrated Fitch ferrets (1.0-1.5 kg) are anesthetized with pentobarbital sodium (30 mg/kg, i.p.). The ventral and dorsal area of the neck is shaved and a 3 cm incision is made. The left jugular vein is exposed and ligated with a silk suture at the cephalic end. The indwelling catheter is constructed of Silastic tubing 18 cm in length (0.020 inch I.D. × 0.037 inch O.D.) with a 2 cm polyethylene sleeve (0.045 inch I.D. × 0.062 inch O.D.) filled with heparin (1000 units/ml) and sealed at the exposed end with a 23 gauge × 1 inch needle crimped at both ends. A small cut is made in the jugular and the catheter inserted, allowing the free end to be delivered through a 13 gauge × 5 cm trochar under the skin and attached to the nape of the neck with a silk suture. The ferrets are housed in individual cages and allowed 2-4 days recovery before testing.

On the test day, the test compounds were administered i.v. (3 mg/ml or 1 ml/kg) via the catheter 5 minutes prior to and 90 minutes after cisplatin. The cisplatin solution was prepared by adding 70° C. physiological saline, stirring and sonicating until dissolved. The resulting solution (4 mg/ml) was maintained at 40° C. and administered i.v. (12 ml/kg) via the catheter. Following administration of cisplatin, the ferrets were observed continuously for four hours and emetic episodes recorded. Two or more emetic episodes within a one-minute period was considered as a single episode.

The ferrets were euthanized with T-61 i.v. at the termination of the experiment, and proper placement of the catheter was verified. The results of the test are shown in Table 1 as the percent protection (graded response) compared to saline treatment. The dosage and number of animals also are shown for each test.

(D) Gastrokinetic Activity

A number of compounds of this invention have been found to enhance contraction of field-stimulated guinea pig ileum preparations. This activity is considered to be correlated with gastrokinetic (prokieetic) activity in vivo, i.e. enhancement of gastric motility and gastric emptying.

Normal, male guinea pigs (Hartley; Charles River) weighing 300-400 g are sacrificed by cervical dislocation. The terminal portion of the ileum was removed after discarding a 10 cm segment nearest to the ileocecal junction. The strips, 3-4 cm in length, were mounted in a 20 ml organ bath containing Krebs physiological buffer solution. The buffer was bubbled with 95% $O_2$-5% $CO_2$ and kept at 37° C. The resting tension was adjusted to 1.0 g, and the tissues were equilibrated without stimulation for 15 minutes. For electrical stimulation, a platinum wire (cathode) was threaded up through the lumen and another platinum wire (anode) was attached to the glass rod that suspended the muscle. Tissues were stimulated coaxially at 1.5 times the voltage necessary to produce maximum twitch height, with single pulses, 0.5 msec in duration, delivered once every 10 seconds. After the 15 minute equilibration period (without stimulation), the stimulator (Grass S88 Stimulator) was turned on and the tissues were allowed to stabilize for approximately 1 hour, or until the twitch height remained constant, with washes every 20 minutes. The contractions of the ileum were recorded isometrically by means of a force displacement transducer (Grass FT03C) and displayed on a Dynograph recorder. Some of the compounds of Formula I which showed increased contractions of field stimulated guinea pig ileum preparations are listed in Table 2, with the average % maximum increase, minimum effective concentration ($\mu$m), effective concentration$_{30}$ ($EC_{30}$) and, in some instances, effective concentration$_{50}$ ($EC_{50}$) ($\mu$M).

TABLE 1

| | Dopaminergic Antagonism and Antiemetic Activity | | | |
|---|---|---|---|---|
| | | Antagonism of | Antagonism of Cisplatin-Induced Emesis in the Ferret | |
| | $^3$H—Spiperone | Apomorphine-Induced | | |
| Compound of Example | Displacement $IC_{50}$ (nm) | Emesis in the Dog $ED_{50}$ (mg/kg, s.c.) | Dose (mg/kg, i.v.) × 2 (Number of Animals = 3) | % Protection |
| 1 | >1000 | >3 | 3 | 76 |
| 2 | >1000 | >3 | 3 | 68 |
| 3 | >1000 | >3 | 3 | 82 |
| 4 | >1000 | >3 | 3 | 100 |
| 5 | >1000 | >3 | 3 | 90 |
| 6 | >1000 | >3 | 3 | 100 |
| 7 | >1000 | >3 | 3 | 95 |
| 8 | >1000 | >3 | 3 | 95 |

TABLE 1-continued

Dopaminergic Antagonism and Antiemetic Activity

| Compound of Example | $^3$H—Spiperone Displacement IC$_{50}$ (nm) | Antagonism of Apomorphine-Induced Emesis in the Dog ED$_{50}$ (mg/kg, s.c.) | Antagonism of Cisplatin-Induced Emesis in the Ferret Dose (mg/kg, i.v.) × 2 (Number of Animals = 3) | % Protection |
|---|---|---|---|---|
| 9 | >1000 | >3 | 3 | 100 |
| 10 | >1000 | >3 | 3 | 100 |
| 11 | >1000 | >3 | 3 | 90 |
| 12 | >1000 | >3 | 3 | 86 |
| 13 | >1000 | >3 | 3 | 90 |
| 14 | >1000 | >3 | 3 | 62 |
| 15 | >1000 | >3 | 3 | 30 |
| 16 | >1000 | >3 | 3 | 21 |
| 18 | >1000 | >3 | 3 | 72 |
| 19 | >1000 | >3 | 3 | 72 |
| 20 | >1000 | >3 | 3 | 50 |
| 21 | >1000 | >3 | 3 | 49 |
| 24 | >1000 | >3 | 3 | 67 |
| 25 | >1000 | >3 | 1 | 58 |
| 26 | >1000 | >3 | 3 | 90 |
| 27 | >1000 | >3 | 1 | 90 |
| 28 | >1000 | >3 | 1 | 82 |
| 29 | >1000 | >3 | 1 | 44 |
| 30 | >1000 | >3 | 3 | 100 |
| 31 | >1000 | >3 | 1 | 67 |
| 32 | >1000 | >3 | 1 | 72 |
| 33 | >1000 | >3 | 1 | 54 |
| 34 | >1000 | >3 | 1 | 54 |
| 35 | >1000 | >3 | 3 | 72 |
| 36 | >1000 | >3 | 3 | 86 |
| 37 | >1000 | >3 | 3 | 57 |
| 38 | >1000 | >3 | 3 | 57 |
| 39 | >1000 | >3 | 3 | 71 |
| 40 | >1000 | >3 | 3 | 62 |
| 41 | >1000 | >3 | 3 | 81 |
| 42 | >1000 | >3 | 3 | 95 |
| 43 | >1000 | >3 | 3 | 67 |
| 44 | >1000 | >3 | 3 | 71 |
| 45 | >1000 | >3 | 3 | 80 |
| 46 | >1000 | >3 | 3 | 76 |
| 47 | >1000 | >3 | 3 | 8 |
| 48 | >1000 | >3 | 3 | 47 |
| 49 | >1000 | >3 | 3 | 62 |
| 50 | >1000 | >3 | 3 | 62 |
| 51 | >1000 | >3 | 3 | 71 |
| 52 | >1000 | >3 | 3 | 95 |
| 53 | >1000 | >3 | 3 | 91 |
| 54 | >1000 | >3 | 3 | 81 |
| 55 | >1000 | >3 | 3 | 66 |
| 56 | >1000 | >3 | 3 | 81 |
| 57 | >1000 | >3 | 3 | 66 |
| 58 | >1000 | >3 | 3 | 66 |
| 59 | >1000 | >3 | 3 | 66 |
| 60 | >1000 | >3 | 3 | 52 |
| 61 | 760 | >3 | 3 | 71 |
| 62 | >1000 | >3 | 3 | 71 |
| Metoclopramide | 310 | 0.5 | 3* | 89 |
| Alizapride | 290 | 0.3 | 3 | 27 |
| Clebopride | 11 | 0.04 | 3 | 70 |
| Domeperidone | 4.1 | 0.2 | 3 | 50 |

*Number of animals = 4

TABLE 2

Gastrokinetic Activity

| Compound of Example | Number of Preparations | Average % Maximum Increase | Minimum Effective Concentration (μm) | EC$_{30}$ (95% C.L.) EC$_{50}$ (95% C.L.) |
|---|---|---|---|---|
| 4 | 4 | 58% at 10 μM | 0.1 | 1.5 (1.1–2.0) 5.2 (3.8–7.8) |
| 14 | 6 | 55% at 30 μM | 0.1 | 4.3 (3.2–5.9) 18 (12–28) |
| 16 | 6 | 72% at 100 μM | 0.03 | 0.5 (0.3–0.9) 3.7 (2.0–9.3) |
| 17 | 5 | 41% at 10 μM | 0.3 | 5.4 (3.6–9.1) 15 (8.8–44) |
| 19 | 6 | 39% at 3 μM | 0.1 | 1.7 (1.2–2.7) 5.9 (3.5–18) |
| 21 | 6 | 88% at 30 μM | 0.1 | 0.57 (0.24–1.0) 2.3 (1.3–4.3) |

TABLE 2-continued

| Compound of Example | Number of Preparations | Gastrokinetic Activity | | |
|---|---|---|---|---|
| | | Average % Maximum Increase | Minimum Effective Concentration (μm) | EC$_{30}$ (95% C.L.) EC$_{50}$ (95% C.L.) |
| 36 | 4 | 55% at 10 μM | 0.1 | 0.5 (0.09–1.4) 4.6 (1.7–56) |
| 37 | 4 | 83% at 300 μM | | 0.72 (0.28–1.4) 6.6 (3.5–1.3) |
| 40 | 6 | 56% at 10 μM | 0.1 | 0.9 (0.5–1.5) 5.5 (3.0–15) |
| 48 | 4 | 47% at 10 μM | 0.1 | 2.3 (1.8–21) 13 (9.4–21) |
| 50 | 4 | 45% at 30 μM | 1.0 | 12 (9–14) 39 (30–55) |
| 51 | 6 | 51% at 10 μM | 0.03 | 0.23 (0.25–0.51) 5.0 (2.0–43) |
| 56 | 4 | 59% at 30 μM | 0.1 | 1.1 (0.59–1.8) 7.3 (4.2–16) |
| 58 | 4 | 72% at 30 μM | 0.3 | 1.5 (0.8–2.5) 5.6 (3.4–10) |
| 59 | 6 | 38% at 10 μM | 1.0 | 5.2 (3.2–11) 20 (10–134) |
| 60 | 6 | 66% at 30 μM | 0.1 | 0.88 (0.58–1.2) 4.8 (3.3–7.4) |
| Metoclopramide | 10 | 62% at 30 μM | 0.03 | 1.6 (1.0–2.4) 11 (7.0–20) |

Tables 1 and 2 show the compounds of Formula I to have useful antiemetic and gastrokinetic activity, while Table 1 shows that the compounds are essentially free of dopaminergic antagonism, thus avoiding the side-effect liabilities of the currently available substituted benzamide antiemetic and gastrokinetic agents.

The compounds of Formula I may be administered either orally, parenterally or by suppository. When utilized as an antiemetic in the case of patients receiving cancer chemotherapeutic agents such as cisplatin, it preferably is given as an intravenous infusion diluted in a larger volume of parenteral solution (such as Dextrose—5% in water, Dextrose —5% in 0.45% sodium chloride, Ringer's Injection or Lactated Ringer's Injection). When utilized as a gastrokinetic agent, the compounds preferably are given orally if the symptoms are not severe. With severe symptoms, therapy preferably should begin with i.m. or i.v. administration until the severe symptoms subside, at which time oral administration may be instituted.

The dosage of the compounds of Formula I depend on the purpose for which they are taken (antiemetic or gastrokinetic), the particular compound administered, the age, weight and general health of the patient, as well as the severity of the malady, and is within the discretion of the physician.

When taken for gastrokinetic purposes, the compounds of Formula I are generally administered at a dosage of from 1 to 100 mg and preferably from 5 to 50 mg, from 2 to 5 times a day and preferably four times a day, e.g. before each meal and at bedtime.

For the prevention of nausea and vomiting associated with emetogenic cancer chemotherapeutic agents, the compounds of Formula I are generally administered (diluted in a larger volume of parenteral solution) at a dosage of from 0.1 to 50 mg/kg and preferably from 0.5 to 10 mg/kg, given several times per day. The particular dose to be used depends on the factors mentioned above, as well as the emetogenicity of the cancer chemotherapeutic agent. In general, the first dose should be given prior to the administration of the cancer chemotherapeutic agent, e.g. 30 minutes, and then every 2-8 hours after administration of the chemotherapeutic agent, until the symptoms of nausea and vomiting subside or become less severe, e.g. for 12 to 24 hours.

Tablets and capsules for oral use preferably are in unit dosage form, and may contain conventional excipients such as binding agents, fillers, tabletting lubricants, disintegrants, wetting agents and the like. The tablets may, if desired, be film coated by conventional techniques. Liquid preparations for oral use may be in the form of aqueous or oily suspensions, solutions, emulsions, syrups or elixirs, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents.

For parenteral administration, the compounds of Formula I are combined with a sterile vehicle. Depending on the vehicle and concentration of active ingredient, the dosage form may be a solution or suspension. The vehicle normally will comprise sterile water, at least in large part, although saline solutions, glucose solutions and the like may be utilized. Injectable suspensions also may be used, in which case conventional suspending agents may be employed. Conventional preservatives, buffering agents and the like also may be added to the parenteral dosage forms.

For solid dosage forms, either the free base or a salt of the compounds of Formula I may be used. In the case of aqueous solutions, either oral or parenteral, it is often preferred to utilize a salt of the compounds of Formula I, due to the usual greater solubility of the salts in aqueous solutions.

It is especially advantageous to formulate the above pharmaceutical compositions in unit dosage form for ease of administration and uniformity of dosage. Unit dosage form refers to physically discrete units suitable as unitary doses, each unit containing a predetermined quantity of active ingredient, calculated to produce the desired effect, in association with the desired pharmaceutical carrier.

This invention also includes pharmaceutical compositions for the alleviation of nausea and vomiting, which comprises an effective antiemetic amount of at least one compound of Formula I, or a salt, hydrate or solvate thereof, plus a pharmaceutically acceptable carrier.

This invention also includes pharmaceutical compositions for the treatment of disorders related to impaired gastric motility, which comprise an effective gastric motility facilitating amount of at least one compound of Formula I, or a salt, hydrate or solvate thereof, and a pharmaceutically acceptable carrier.

This invention also relates to a method of alleviating nausea and vomiting in a warm-blooded mammal in need thereof, which comprises administering to said mammal an effective antiemetic amount of at least one compound of Formula I, or a salt, hydrate or solvate thereof, in a pharmaceutically acceptable carrier.

This invention also relates to a method of treating disorders related to impaired gastric motility in a warm-blooded mammal, which comprises administering to said mammal an effective gastric motility facilitating amount of at least one compound of Formula I, or a salt, hydrate or solvate thereof, in a pharmaceutically acceptable carrier.

As used herein and in the claims, the term "(lower)alkyl" means a straight or branched alkyl chain containing from 1 to 6 carbon atoms. Similarly, the terms "(lower)alkenyl" and "(lower)alkynyl" refer to alkenyl or alkynyl chains containing from 2 to 6 carbon atoms. All temperatures given herein are in degrees Centigrade.

Preparation No. 1

4-Amino-5-chloro-N-[2-(diethylamino)ethyl]-2-hydroxybenzamide (A)

4-Amino-5-chloro-N-[2-(diethylamino)ethyl]-2-hydroxybenz amide Hydrochloride

To a cooled (<10°) stirred suspension of sodium hydride (57.44 g of 60%, 1.436 moles) in DMF (1275 ml) was added dropwise a cold solution of ethanethiol (89.22 g, 1.436 moles) in DMF (250 ml). After hydrogen evolution had ceased 4-amino-5-chloro-N-[2-(diethylamino)ethyl]-2-methoxybenzamide (287.0 g, 0.957 moles) (prepared according to U.S. Pat. No. 3,357,978 [1965]) was added and the mixture was heated in an oil bath at 100°-105° for 90 minutes. The solvent was removed in vacuo and the residue partitioned between methylene chloride (800 ml) and water (400 ml). The aqueous layer was washed with another portion of methylene chloride and the combined organic extracts were backwashed with water (150 ml). The combined aqueous phase was cooled in an ice bath and treated with concentrated hydrochloric acid (200 ml). After 20 minutes the precipitate was collected by filtration, sucked briefly on the filter, slurried with methanol (500 ml) and again filtered. The product was dried in vacuo to give 302.3 g (98%) of the title compound as a light beige solid, mp 235°-237°.

Anal. Calc'd. for $C_{13}H_{20}ClN_3O_2 \cdot HCl$: C, 48.46; H, 6.57; N, 13.04; Cl, 22.00. Found: C, 47.67; H, 6.73; N, 12.84; Cl, 21.43.

(B)

4-Amino-5-chloro-N-[2-(diethylamino)ethyl]-2-hydroxybenz amide

To stirred concentrated ammonium hydroxide (6 ml) was added 4-amino-5-chloro-N-[2-(diethylamino)ethyl]-2-hydroxybenzamide hydrochloride (3.0 grams, 0.0093 mole) and the mixture stirred an additional five minutes followed by the addition of three to four ml of water and another five minute stirring. After filtration the solid was washed two times with three ml of water each time to give, after drying, 2.37 g of the title compound, mp 134°-136° C. NMR spectrum (90 MHz) in CDCl$_3$ gave the following resonances δ: 7.26 (s, 1H); 6.90 (s, 1H); 6.14 (s, 1H); 4.39 (s, 2H); 3.40 (s, 2H); 2.60 (multiplet, 6H); 1.06 (t, 6H).

Preparation No. 2

4-Amino-5-chloro-N-[2-(diethylamino)ethyl]-2-hydroxybenzamide (Alternate Procedure)

A mixture of 4-amino-5-chloro-N-[2-(diethylamino)ethyl]-2-methoxybenzamide (29.5 g, 0.1 mole), sodium hydroxide pellets (4.0 g, 0.1 mole) and 1,2-propanediol (70 ml) was stirred and heated under reflux for 20 hours followed by concentration in vacuo. The residue was treated with 1N HCl (100 ml) and again concentrated in vacuo. The residue was chromatographed on silica using methylene chloride (90), methanol (10), ammonia (0.5) solvent system. The appropriate fractions were combined and concentrated in vacuo and the residue crystallized from ether to give 9.3 g of product. This was dissolved in hot water, and the solution filtered over charcoal. The filtrate was cooled and filtered to give 6.7 g of tan colored title compound, mp 126°-7° (U.S. Pat. No. 3,357,978 reports mp 160°).

Anal. Calc'd. for $C_{13}H_{20}ClN_3O_2$: C, 54.64; H, 7.05; N, 14.70. Found: C, 54.44; H, 7.15; N, 14.65.

Preparation No. 3

Tetra-n-butyl ammonium salt of 4-amino-5-chloro-N-[2-(diethylamino)ethyl]-2-hydroxybenzamide A solution of 4-amino-5-chloro-N-[2-(diethylamino)ethyl]-2-hydroxybenzamide hydrochloride (10 g, 0.031 mmole), 5 g sodium hydroxide and 100 ml water was treated with tetra-n-butylammonium hydrogen sulfate (10.6 g, 0.031 mmole) with stirring. The crystals were collected, washed with water and dried (14.7 g, 87%). Recrystallization from ethyl acetate gave the title compound containing one-half mole of water, mp. 136.5°-138.5°.

Anal. Calc'd. for $C_{29}H_{55}ClN_4O_2 \cdot 0.5\ H_2O$: C, 64.95; H, 10.53; N, 10.44; H$_2$O, 1.71. Found: C, 65.06; H, 10.42; N, 10.40; H$_2$O, 1.41.

EXAMPLE 1

4-Amino-5-chloro-N-[2-(diethylamino)ethyl]-2-(2-methoxyethoxy)benzamide

A mixture of 4-amino-5-chloro-N-[2-(diethylamino)ethyl]-2-hydroxybenzamide hydrochloride (2.50 g, 7.76 mmoles), 2-chloro-ethylmethylether (1.47 g, 15.5 mmoles), potassium carbonate (2.14 g, 15.5 mmoles) and sodium bromide (0.80 g, 7.76 mmoles) in 40 ml of dimethylformamide (DMF) was stirred at reflux for four hours. The DMF was removed under vacuum and the residue was redissolved in methylene chloride and washed with water and dilute NaOH. The solvent was evaporated and the product was chromatographed using a gradient elution of methanol-methylene chloride containing 0.25% NH$_4$OH. The appropriate fractions were combined and evaporated to yield 2.34 g (87.6%) of cream-colored solid. Recrystallization of the residue from ethyl acetate gave the title compound as a white solid, mp 108°-110.5°. The NMR spectrum (90MHz) in CDCl₃ gave the following resonances: δ 8.19 (s, 1H); 6.35 (s, 1H); 4.5 (bs, 2H); 4.2 (m, 2H); 3.8 (m, 2H); 3.5 (m, 2H); 3.49 (s, 3H); 2.59 (m, 6H); 1.02 (t, 6H).

Anal. Calc'd. for $C_{16}H_{26}ClN_3O_3$: C, 55.89; H, 7.62; N, 12.22 Cl, 10.31. Found: C, 55.66; H, 7.66; N, 12.15 Cl, 10.35.

EXAMPLE 2

4-Amino-5-chloro-N-[2-(diethylamino)ethyl]-2-(2-hydroxyethoxy)benzamide

The general procedure of Example 1 was repeated, except that the 2-chloroethylmethyl ether utilized therein was replaced by 1.50 g (18.62 mmoles) of 2-chloroethanol. The crude product was purified by flash chromatography on 50 g of silica gel (230–400 mesh) using a gradient elution of methanol-methylene chloride containing 0.25% ammonia. The appropriate fractions were combined and the solid residue was recrystallized from acetonitrile to yield 1.30 g (42.5%) of the title compound, mp 144°–146.5°. The NMR spectrum (90 MHz) in DMSO/CDCl₃ gave the following resonances: δ 8.1 (s, 1H); 6.4 (s, 1H); 4.75 (bs, 2H); 4.05 (m, 4H); 3.6 (m, 2H); 2.7 (m, 6H); 1.1 (t, 6H).

Anal. Calc'd. for $C_{15}H_{24}ClN_3O_3$: C, 54.62; H, 7.33; N, 12.74 Cl, 10.31. Found: C, 54.67; H, 7.88; N, 12.92 Cl, 10.69.

EXAMPLE 3

4-Amino-5-chloro-N-[2-(diethylamino)ethyl]-2-(2,2-dimethoxyethoxy)benzamide

A mixture of 4-amino-5-chloro-N-[2-(diethylamino)ethyl]-2-hydroxybenzamide hydrochloride (8.06 g, 0.025 mole), chloroacetaldehyde dimethyl acetal (6.23 g; 0.05 mole), potassium carbonate (6.91 g, 0.05 moe) and sodium bromide (2.57 g, 0.025mole) in 100 ml of dry DMF was stirred at reflux for 8 hours. After four hours at reflux an additional amount of the alkylating agent (6.23 g, 0,05 mole) was added. The mixture was filtered and the DMF was removed under vacuum. The oily residue was redissolved in methylene chloride and washed sequentially with water, aqueous 1.0N NaOH, water and saturated NaCl solution. The solvent was evaporated and the product was further purified by chromatography using a gradient elution of methanol-methylene chloride containing 0.25% of ammonia. The appropriate fractions were combined and evaporated to give a yellow residue. Recrystallization from ethyl acetate-petroleum ether yielded the title compound as a white solid; wt. 5.5 g (59.8%), mp 64°–67°. The NMR spectrum (90 MHz) in CDCl₃ gave the following resonances: δ 8.19 (s, 1H); 6.32 (s, 1H); 4.83 (t, 2H); 4.42 (bs, 2H); 4.08 (d, 2H); 3.55 (m, 2H); 3.50 (m, 2H); 2.41 (m, 6H); 1.1 (t, 6H).

Anal. Calc'd. for $C_{17}H_{28}ClN_3O_4$: C, 54.61; H, 7.55; N, 11.24 Cl, 9.48. Found: C, 54.21; H, 7.42; N, 11.07 Cl, 10.34.

EXAMPLE 4

4-Amino-5-chloro-N-[2-(diethylamino)ethyl]-2-[(2-methoxyethoxy)methyloxy]benzamide To a well stirred suspension of sodium hydride (0.34 g of 60%, 0.014 mole) in 5 ml dry DMF was added a solution of 4-amino-5-chloro-N-[2-(diethylamino)ethyl]-2-hydroxy benzamide (3.57 g, 0.012 mole) in 15 ml dry DMF at room temperature over 18 minutes. The mixture was then stirred an additional hour giving essentially a clear solution. To this was added dropwise a solution of 2-methoxyethoxymethyl chloride (1.74 g, 0.014 mole) in 5 ml dry DMF. After an additional four hours at ambient temperature, the mixture was concentrated in vacuo, and the residue partitioned between water (200 ml) and methylene chloride (75 ml). The aqueous phase was extracted twice with 75 ml portions of methylene chloride. After combining, the organic phase was washed three times with 50 ml of 10% aqueous sodium hydroxide and three times with brine; dried over sodium sulfate, filtered, concentrated in vacuo, to give 4.26 grams of residue. Crystallization from ether gave 2.53 grams of the title compound, mp 79°–81° C. The NMR spectrum (90 MHz) in CDCl gave the following resonances: δ 8.18 (s, 2H); 6.61 (s, 1H); 5.40 (s, 2H); 4.40 (s, 2H); 3.84 (m, 2H); 3.50 (m, 4H); 3.44 (s, 3H); 2.56 (m, 6H); 1.04 (t, 6H).

Anal. Calc'd. for $C_{17}H_{28}ClN_3O_4$: C, 54.60; H, 7.56; N, 11.24. Found: C, 54.16; H, 7.75; N, 11.16.

EXAMPLE 5

4-Amino-5-chloro-N-[2-(diethylamino)ethyl]-2-(2-propanon-1-yl)oxybenzamide

To a stirred suspension of 4-amino-5-chloro-N-[2-(diethylamino)ethyl]-2-hydroxybenzamide hydrochloride (5.0 g, 16 mmoles) and potassium carbonate (10.62 g, 77 mmoles) in DMF (25 ml) was added chloroacetone (2.32 g of 90%, 22 mmoles) and the mixture stirred vigorously for 5 hours, followed by pouring into water (130 ml) and filtration to give, after drying, 4.57 g of crude product. This was dissolved in methylene chloride and filtered over a short alumina column, followed by concentration and recrystallization of the residue from toluene to give 4.16 g (78%) of the title compound as white solid, mp 105°–106.5°. The NMR (90 MHz) in CDCl₃ gave the following resonances: ε 8.44 (s, 1H); 8.24 (s, 1H); 6.16 (s, 1H); 4.72 (s, 2H); 4.4 (s, 2H); 3.6 (m, 2H); 2.68 (m, 6H); 2.28 (s, 3H); 1.08 (t, 6H).

Anal. Calc'd. for $C_{16}H_{24}ClN_hd 3O_3$: C, 56.21; H, 7.08; N, 12.29 Cl, 10.37. Found: C, 56.14; H, 6.97; N, 12.29 Cl, 10.29.

EXAMPLE 6

4-Amino-2-(2-phenyl-2-oxoethoxy)-5-chloro-N-[2-(diethylamino)ethyl]benzamide To a stirred suspension of sodium hdride (320 mg of 60%, 8 mmoles, washed with n-pentane) in DMF (15 ml) was added 4-amino-5-chloro-N-[2-(diethylamino)ethyl]-2-hydroxybenzamide hydrochloride (1.289 g, 4 mmoles) and the mixture stirred for 20 minutes followed by addition of chloroacetophenone (619 mg, 4 mmoles). The mixture was stirred 4 hours, poured into ice-cold water (50 ml) whereupon a solid separated out. This was isolated by filtration, dried and recrystallized from methanol to give 810 mg (50%) of the title compound as white solid mp 153°–4°. The NMR spectrum (90 MHz) in CDCl₃ gave the following resonances: δ8.64 (bs, 1H); 8.2 (s, 1H); 8 (m, 2H); 7.6 (m, 3H); 6.22 (s, 1H); 5.36 (s, 2H); 4.4 (s, 2H); 3.52 (m, 2H); 2.64 (m, 6H); 1.01 (m, 6H).

Anal. Calc'd for $C_{21}H_{26}ClN_3O_3$: C, 62.45; H, 6.49; N, 10.40 Cl, 8.78. Found: C, 62.54; H, 6.39; N, 10.83 Cl, 8.68.

EXAMPLE 7

(A)

4-Amino-2-(butan-2-on-3-yl)oxy-5-chloro-N-[2-(diethylamino)ethyl]benzamide

To a stirred suspension of sodium hydride (40 mg of 60%, 1 mmole, washed with n-pentane) in DMF (2 ml) was added 4-amino-5-chloro-N-[2-(diethylamino)ethyl]-2-(2-propanon-1-yl)oxybenzamide, prepared in Example 5, (0.349 g, 1 mmole) under nitrogen. The mixture was stirred until evolution of hydrogen subsided, when iodomethane (0.07 ml, 160 mg, 1.1 mmol) was added and stirring continued for 1 hour. The mixture was partitioned between water and methylene chloride, and the organic phase washed with water, dried, concentrated and the residue chromatographed on deactivated silica using methylene chloride (100), methanol (4.5), ammonia (0.5) solvent system. The appropriate fractions were combined to give 160 mg of the title compound as a heavy oil. The NMR spectrum (90 MHz) in CDCl$_3$ gave the following resonances: δ 8.24 (s, superimposed over broad singlet, 2H); 6.08 (s, 1H); 4.70 (q, J=5.4 Hz, 1H); 4.44 (s, 2H); 3.56 (m, 2H); 2.62 (m, 6H); 2.2 (s, 3H); 1.6 (d, J=5.4 Hz, 3H); 1.04 (t, 6H).

(B)

4-Amino-2-(butan-2-on-3-yl)oxy-5-chloro-N-[2-(diethylamino)ethyl]benzamide hydrochloride To a stirred suspension of 4-amino-5-chloro-N-[2-(diethylamino)ethyl]-2-hydroxybenzamide hydrochloride (1.94 g, 6 mmoles) and potassium carbonate (4.16 g, 30 mmoles) in DMF (10 ml) was added 3-chloro-2-butanone (0.95 g, 8.9 mmoles) and the mixture stirred for 3 hours, followed by pouring into water and extraction with methylene chloride. The extract was washed well with water, dried and concentrated in vacuo. The residue was dissolved in 1-propanol and treated with 2N HCl followed by concentration to give an oily residue. This was crystallized from acetone and the product recrystallized from 2-propanol to give 1.4 g of the title compound mp 98° C. as the hemihydrate.

Anal. Calc'd. for C$_{17}$H$_{26}$ClN$_3$O$_3$. HCl 0.5H$_2$O: C, 51.00; H, 6.80; N, 10.50; Cl, 17.71. Found: C, 51.26; H, 6.86; N, 10.51; Cl, 17.38.

(C)

4-Amino-2-(butan-2-on-3-yl)oxy-5-chloro-N-[2-(diethylamino)ethyl]benzamide Hydrochloride To a stirred suspension of 4-amino-5-chloro-N-[2-(diethylamino)ethyl]2-hydroxybenzamide hydrochloride (19.4 g, 60 mmoles), potassium carbonate (41.6 g, 0.3 moles) and sodium iodide (10 g) in DMF (100 ml) was added 3-chloro-2-butanone (9.5 g, 89 mmoles) and the mixture vigorously stirred and heated to 70°-80° for 2 hours followed by cooling and partition between water and methylene chloride. The organic phase was washed with water, dried and concentrated. The residue was treated with 2N HCl and azeotroped with n-propanol, and crystallized from acetone to give 19.0 g (81%) of the title compound mp 177°-179°.

EXAMPLE 8

4-Amino-5-chloro-N-[2-(diethylamino)ethyl]-2-[(3-methyl)-5-hexen2-on-3-yl]oxybenzamide To a stirred suspension of sodium hydride (0.2 g of 60%, 5 mmoles, washed with n-pentane) in DMF (10 ml) was added dropwise a solution of 4-amino-2-(butan-2-on-3-yl)oxy-5-chloro-N-[2-(diethylamino)ethyl]benzamide (1.78 g, 5 mmoles) in DMF (10 ml). After hydrogen evolution subsided, allyl bromide (690 mg, 5.7 mmoles) was added and the mixture stirred for 72 hours, followed by partition between water and methylene chloride. The organic phase was washed with water, dried and concentrated. The residue was chromatographed on deactivated silica, using methylene chloride (100), methanol (4), ammonia (0.5). The appropriate fractions were combined to give 0.58 g of crude product as a heavy oil. This was crystallized from ether to give the title compound as a white solid, mp 138°-140°. The NMR spectrum (90 MHz) in CDCl$_3$ gave the following resonances: δ 8.24 (s, 1H); 8.0 (bs, 1H); 5.92 (s, 1H); 5.9-5.0 (m, 4H); 4.38 (bs, 2H); 3.58 (m, 2H); 3.0-2.3 (m, 8H); 2.28 (s, 3H); 1.62 (s, 3H); 1.04 (t, 6H).

Anal. Calc'd. for C$_{20}$H$_{30}$ClN$_3$O$_3$: C, 60.67; H, 7.68; N, 10.61. Found: C, 60.34; H, 7.67; N, 10.54.

EXAMPLE 9

4-Amino-5-chloro-2-(cyclohexanon-2-yl)oxy-N-[2-(diethylamino)ethyl]benzamide

A suspension of 4-amino-5-chloro-N-[2-(diethylamino)ethyl]-2-hydroxybenzamide hydrochloride (6.4 g, 20 mmoles) and potassium carbonate (13.8 g, 0.1 mole) in DMF (34 ml) and 2-chlorocyclohexanone (3.8 g, 28.6 mmoles) was stirred for 4 days, followed by partition between water and methylene chloride. The organic phase was washed well with water, dried and concentrated. The residue was chromatographed on deactivated silica using methylene chloride (100), methanol (4), ammonia (0.5) as the solvent system. The appropriate fractions were combined and further purified by low pressure liquid chromatography to give 1.0 g of the title compound as a colorless foam. The NMR spectrum (90 MHz) in CDCl$_3$ gave the following resonances: δ 8.4 (bs, 1H); 8.16 (s 1H); 6.14 (s, 1H); 4.7 (m, 1H); 4.3 (s, 2H); 3.56 (q, J=7.2 Hz, 2H); 2.62 (m, 6H); 2.3-1.4 (m, 8H); 1.04 (t, J=7.2 Hz, 6H).

Anal. Calc'd. for C$_{19}$H$_{28}$ClN$_3$O$_3$: C, 59.75; H, 7.39; N, 11.00; Cl, 9.29. Found: C, 59.40; H, 7.32; N, 10.94; Cl, 8.99.

EXAMPLE 10

4-Amino-5-chloro-N-[2-(diethylamino)ethyl]-2-[(2-hydroxyimino)propan-1-yl]oxybenzamide A mixture of 4-amino-5-chloro-N-[2-(diethylamino)ethyl]-2-propanon-1-yl)oxybenzamide (1.0 g, 2.9 mmoles) and hydroxylamine hydrochloride (0.3 g, 4.3 mmoles) in methanol (20 ml) was heated under reflux for 10 minutes, followed by concentration in vacuo. The residue was partitioned between aqueous sodium carbonate and methylene chloride. The organic phase was dried and concentrated, and the residue dissolved in methanol, treated with charcoal and filtered. The filtrate was concentrated in vacuo and the residue crystallized from ethyl acetate-n-pentane to give 0.58 g (56%) of the title compound containing 0.25 mole of water of crystallization, mp 112°-113°. The NMR spectrum (90 MHz) in CDCl$_3$ gave the following resonances: δ 9.16 (s, 1H); 8.32 (s, 1H); 6.36 (s, 1H); 4.72 (s, 2H); 4.36 (s, 2H); 3.68 (m, 2H); 2.68 (m, 6H); 1.92 (s, superimposed over a broad absorption, 4H); 1.12 (t, 6H).

Anal. Calc'd. for $C_{16}H_{25}N_4O_3 \cdot \frac{1}{4}H_2O$: C, 53.18; H, 7.11; N, 15.50; Cl, 9.80. Found: C, 53.18; H, 7.01; N, 15.36; Cl, 9.52.

EXAMPLE 11

4-Amino-5-chloro-N-[2-(diethylamino)ethyl]-2-[(2-methoxyimino)-propan-1-yl]oxybenzamide The general procedure of Example 10 was repeated except that the hydroxylamine hydrochloride used therein was replaced by methoxyamine hydrochloride, and the reaction was conducted at ambient temperature (16 hours) to give the title compound in 70% yield a as white solid mp 121°–123° from methylene chloride-n-pentane. The NMR spectrum (90 MHz) in CDCl$_3$ was similar to that of Example 10 with an additional singlet at δ3.92 (3H).

Anal. Calc'd. for $C_{17}H_{27}ClN_4O_3$: C, 55.05; H, 7.34; N, 15.11; Cl, 9.56. Found: C, 54.69; H, 7.48; N, 14.92; Cl, 9.47.

EXAMPLE 12

4-Amino-5-chloro-N-[2-(diethylamino)ethyl]-2-(2-hydroxypropan-1-yl)oxybenzamide

A mixture of 4-amino-5-chloro-N-[2-(diethylamino)ethyl]-2-(2-propanon-1-yl)oxybenzamide (1.28 g, 3.7 mmoles) and sodium borohydride (80 mg, 2.1 mmoles) in absolute ethanol (15 ml) was refluxed for 30 minutes, followed by addition of another 50 mg (1.3 mmole) of sodium borohydride and reflux for 10 minutes. The mixture was acidified with 2N HCl and concentrated in vacuo. The residue was partitioned between water and ether, and the ether layer was discarded. The aqueous layer was made basic with $N_2CO_3$ and the solid filtered off to give 0.80 g (77%) of the title compound mp 149°–150°. The NMR spectrum (90 MHz) in CDCl$_3$ gave the following resonances: δ8.48 (bs, 1H); 8.16 (s, 1H); 6.28 (s, 1H); 4.4–3.4 (m, 7H); 2.64 (m, 6H); 1.26 (d, J=7.5Hz, 3H); 1.08 (t, 3H).

Anal. Calc'd. for $C_{16}H_{26}ClN_3O_3$: C, 55.88; H, 7.62; N, 12.22; Cl, 10.31. Found: C, 56.08; H, 7.65; N, 12.05; Cl, 9.80.

EXAMPLE 13

4-Amino-5-chloro-2-cyanomethoxy-N-[2-(diethylamino)ethyl]-benzamide

To a stirred suspension of sodium hydride (420 mg of 60%, 10.5 mmoles, washed with n-pentane) in 10 ml DMF was added 4-amino-5-chloro-N-[2-(diethylamino)ethyl]-2-hydroxybenzamide hydrochloride (1.612 g, 5 mmoles) and the mixture stirred for 20 minutes, followed by cooling (ice bath) and addition of chloroacetonitrile (418 mg, 5.5 mmoles) and sodium bromide (100 mg). The mixture was stirred in the cold for 1 hour and at ambient temperature for 16 hours, followed by pouring into a mixture of water and ice, and filtration of the resulting solid. The product was dissolved in methylene chloride and filtered over alumina, followed by concentration in vacuo to give crude product. This was recrystallized from methanol to give 930 mg (57%) of the title-compound as white crystalline solid mp 188°–189°. The NMR spectrum (90 MHz) in CDCl$_3$ gave the following resonances: δ8.1 (s, 1H); 7.78 (bs, 1H); 6.44 (s, 1H); 4.84 (s, 2H); 4.60 (s, 2H); 3.43 (m, 2H); 2.59 (m, 6H); 1.02 (t, 6H).

Anal. Calc'd. for $C_{15}H_{21}ClN_hd 4O_2$: C, 55.47; H, 6.52; N, 17.25; Cl, 10.92. Found: C, 55.85; H, 6.59; N, 16.95; Cl, 10.97.

EXAMPLE 14

4-Amino-5-chloro-N-[2-(diethylamino)ethyl]-2-(1-cyano)ethoxybenzamide

A mixture of 4-amino-5-chloro-N-[2-(diethylamino)ethyl]-2-hydroxybenzamide hydrochloride (4.036 g, 12.5 mmoles), potassium carbonate (8.56 g, 62 mmoles), 2-chloropropionitrile (1.57 g, 17.54 mmoles) and sodium iodide (300 mg) in DMF (18 ml) was stirred and heated at 50° for 20 hours, followed by pouring into ice-water and filtration to give crude solid. This was dissolved in methylene chloride and filtered over a short alumina column. The filtrate was concentrated and the residue recrystallized from methylene chloride-ether to give 3.57 g (84.4%) of the title compound mp 139°–140°. The NMR spectrum (90 MHz) in CDCl$_3$ gave the following resonances: δ8.2 (s, 1H); 7.75 (bs, 1H); 6.28 (1, 1H); 4.97 (q, J=7.0 Hz, 1H); 4.5 (bs, 2H); 3.54 (m, 2H); 2.6 (m, 6H); 1.88 (d, J=7.0 Hz, 3H); 1.02 (t, 6H).

Anal. Calc'd. for $C_{16}H_{23}ClN_4O_2$: C, 56.71; H, 6.84; N, 16.53; Cl, 10.46. Found: C, 56.63; H, 6.96; N, 16.53; Cl, 9.64.

EXAMPLE 15

4-Amino-5-chloro-N-[2-(diethylamino)ethyl]-2-(2-methoxy-2-oxoethoxy)benzamide

To a stirred suspension of sodium hydride (420 mg of 0%, 10.5 mmoles) in DMF (10 ml) was added 4-amino-5-chloro-N-[2-(diethylamino)ethyl]-2-hydroxybenzamide hydrochloride (1.612 g, mmoles) and the mixture stirred for 20 minutes, followed by cooling (ice water) and addition of methyl bromoacetate (832 mg, 5.44 mmoles). The mixture was stirred for 20 minutes in the cold and another 10 minutes at ambient temperature followed by pouring into 70 ml of ice-cold water. A separated solid was filtered and dried to give 1.58 g of crude product mp 92°–94°. This was recrystallized from methylene chloride-ether to give 1.21 g of the title compound as a white crystalline solid, mp 94°–95° (67.6% yield). The NMR spectrum (90 MHz) in CDCl$_3$ gave the following resonances: δ8.2 (s, 1H); 6.16 (s, 1H); 4.7 (s, 2H); 4.40 (bs, H); 3.86 (s, 3H); 3.54 (m, 2H); 2.6 (m, 6H); 1.04 (t, 6H).

Anal. Calc'd. for $C_{16}H_{24}ClN_3O_4$: C, 53.70; H, 6.76; N, 11.47; Cl, 9.82. Found: C, 53.57; H, 6.78; N, 11.48; Cl, 9.91.

EXAMPLE 16

4-Amino-2-(2-amino-2-oxoethoxy)-5-chloro-N-[2-(diethylamino)ethyl]benzamide Acetate Monohydrate A well stirred mixture of 4-amino-5-chloro-N-[2(diethylamino)ethyl]-2-hydroxybenzamide hydrochloride (2.0 g, 6.2 mmoles), potassium carbonate (2.57 g, 18.6 mmoles), sodium iodide (0.93 g, 6.8 mmoles) and 2-chloroacetamide (0.64 g, 6.8 mmoles) was heated at 75° for 3 hours. The mixture was then evaporated in vacuo and the residue partitioned between water and methylene chloride. The aqueous phase was extracted twice with methylene chloride, and the combined extracts treated with an excess of acetic acid followed by concentration in vacuo. The semi-solid residue was treated with methylene chloride (150 ml) and filtered to give a colorless solid. This was recrystallized from acetonitrile to give 1.04 g (41%) of the title compound as an off-white solid, mp 116°–125°. The NMR spectrum (90 MHz) in D$_2$O gave the following resonances: δ7.8 (s, 1H); 6.26 (1H, s); 4.8 (s, 2H); 3.8 (m, 2H); 3.3 (m, 6H); 1.95 (s, 3H); 1.3 (t, 6H).

Anal. Calc'd. for C$_{16}$H$_{23}$ClN$_4$O$_3$·CH$_3$CO$_2$H·H$_2$O: C, 48.51; H, 6.94; N, 13.31; Cl, 8.43. Found: C, 48.37; H, 6.88; N, 13.26; Cl, 8.32.

EXAMPLE 17

4-Amino-5-chloro-N-[2-(dimethylamino)ethyl]-2-hydroxybenzamide

The general procedure of Preparation 1A was repeated except that the 4-amino-5-chloro-N-[2-(diethylamino)ethyl]-2-methoxybenzamide utilized therein was replaced by 4-amino-5-chloro-N-[2-(dimethylamino)ethyl]-2-methoxybenzamide (prepared according to U.K. Patent Specification No. 1,793,771). The solvent (DMF) was removed in vacuo, and the residue treated with water and methylene chloride saturated with carbon dioxide, concentrated, and the crude product isolated in 89% yield by extraction with ethanol. A sample was chromatographed on a silica gel column using methylene chloride (97), methanol (3), ammonia (0.3) solvent system. The appropriate fractions were combined and concentrated in vacuo. The residue was crystallized from methanol to give the title compound as a colorless solid, mp. 163°–165°.

Anal. Calc'd. for C$_{11}$H$_{16}$ClN$_3$O$_2$: C, 51.26; H, 6.62; N, 16.31; Cl, 13.76. Found: C, 51.46; H, 6.35; N, 16.12; Cl, 13.60.

EXAMPLE 18

4-Amino-5-chloro-N-[2-(diethylamino)ethyl]-2-(2,2-dimethyl-1,3-dioxalan-4-yl)methoxybenzamide A mixture of 4-amino-5-chloro-N-[2-(diethylamino)ethyl]-2-hydroxybenzamide hydrochloride (3.22 g, 10 mmoles), 4-chloromethyl-2,2-dimethyl-1,3-dioxalane (1.65 g, 10 mmoles), potassium carbonate (2.76 g, 20 mmoles), sodium bromide (1.03 g, 10 mmoles), and 40 ml DMF was heated at reflux for 20 hours. The DMF was removed at reduced pressure. The residue was treated with water and extracted with methylene chloride to give a gum. This material was purified using HPLC [Waters prep 500, silica cartridge, methylene chloride-2-propanol-concentrated ammonia 100:1:0.5 for elution]. Combination of the appropriate fractions gave the title compound as a crystalline solid (1.8 g), mp. 76°–78°.

Anal. Calc'd. for C$_{19}$H$_{30}$ClN$_3$O$_4$: C, 57.06; H, 7.56; N, 10.51; Cl, 8.87. Found: C, 56.65; H, 7.69; N, 10.46; Cl, 8.53.

EXAMPLE 19

4-Amino-5-chloro-N-[2-(diethylamino)ethyl]-2-(3-methylisoxazol-5-yl)methoxybenzamide A solution of the tetrabutylammonium salt of 4-amino-5-chloro-N-[2-(diethylamino)ethyl]-2-hydroxybenzamide (4.82 g, 9.14 mmoles) in 50 ml acetonitrile was treated with 5-bromomethyl-3-methylisoxazole and stirred for 1.5 hours. The crystalline product was collected and dried (2.53 g). A second crop was obtained by concentration of the filtrate and crystallization of the residue from ethyl acetate (0.51 g, 87% yield). The analytical sample was recrystallized from ethyl acetate, mp. 109°–111°.

Anal. Calc'd. for C$_{18}$H$_{25}$ClN$_4$O$_3$: C, 56.76; H, 6.62; N, 14.71; Cl, 9.31. Found: C, 56.78; H, 6.90; N, 14.97; Cl, 9.40.

EXAMPLE 20

4-Amino-5-chloro-N-[2-(diethylamino)ethyl]-2-[2-(methylthio)ethoxy]benzamide A stirred mixture of 4-amino-5-chloro-N-[2-(diethylamino)ethyl]-2-hydroxybenzamide hydrochloride (10.0 g, 31.06 mmoles) (from Preparation No. 1A), anhydrous potassium carbonate (12.84 g, 93.16 mmoles), sodium iodide (4.66 g, 31.06 mmoles) and 2-chloroethyl methyl sulfide (3.70 ml, 4.10 g, 37.26 mmoles) in 60 ml of dry DMF was refluxed for 10 hours. The solvent was evaporated under reduced pressure and the dark semi-solid was partitioned between water and methylene chloride. Sodium hydroxide solution was added to bring the pH of the aqueous layer to 14. The mixture was shaken well and the layers were separated. The aqueous layer was extracted with 3 portions of methylene chloride. The combined organic solutions were dried over MgSO$_4$ and evaporated. The solid obtained was dissolved in 100 ml of warm acetonitrile. The solution was treated with Darco G-60, filtered, evaporated to 30 ml, and stored at −15°. The solid was filtered to give 3.56 g (32%) of the title compound as off-white crystals, mp. 118°–120°.

Anal. Calc'd. for C$_{16}$H$_{26}$ClN$_3$O$_2$S: C, 53.39; H, 7.28; N, 11.67; Cl, 9.85; S, 8.91. Found: C, 53.60; H, 7.39; N, 11.69; Cl, 9.47; S, 9.43.

EXAMPLE 21

4-Amino-5-chloro-N-[2-(diethylamino)ethyl]-2-[2-(methylsulfinyl)ethoxy]benzamide To a stirred solution of 4-amino-5-chloro-N-[2(diethylaxino)ethyl]-2-[2-(methylthio)ethoxy]benzamide (1.0 g, 2.28 mmoles) (prepared in Example 20) and 1.4N HCl solution (3.97 ml, 5.56 mmoles) in 15 ml of H$_2$O at 0°–5°, was added sodium metaperiodate (0.625 g, 2.92 mmoles). The mixture, which soon began to darken, was stirred at 0°–5° for 2 hours. The mixture was then diluted to 50 ml and made alkaline (pH=12) with NaOH solution. Methylene chloride (50 ml) was added, the mixture was shaken well, and the layers were separated. The aqueous layer was extracted with 3 portions of methylene cloride and the combined organic solutions were dried (anhydrous MgSO$_4$) and evaporated. A dark oil (0.96 g) which solidified upon standing was obtained. The crude product was flash chromatographed on silica, eluting with CH$_2$CL$_2$:CH$_3$OH:NH$_4$OH, 80:20:0.5. Appropriate fractions were combined and evaporated to give 0.80 g (77%) of the title compound as a yellow resin which crystallized upon standing, mp. 110°–114°.

Anal. Calc'd. for C$_{16}$H$_{26}$ClN$_3$O$_3$S: C, 51.12; H, 6.97; N, 11.18; Cl, 9.43; S, 8.53. Found: C, 50.42; H, 6.94; N, 10.91; Cl, 9.94; S, 8.30.

EXAMPLE 22

4-Amino-2-(2-butanon-3-yl)oxy-5-chloro-N-[2-(diethylamino)ethyl]benzamide hydrochloride A solution of the tetra-n-butylammonium salt of 4-amino-5-chloro-N-[2-(diethylamino)ethyl]-2-hydroxybenzamide (0.53 g, 1.0 mmole) in acetonitrile (6 ml) was treated with 3-chloro-2-butanone (0.11 ml, 0.12 g, 1.1 mmole) and stirred at 20° for 16 hours. After removal of the acetonitrile at reduced pressure, the residue was treated with 10 ml water and extracted with ethyl acetate. The extracts were washed with dilute sodium carbonate, dried and concentrated to leave an oil which was converted to a monohydrochloride salt with 1.0 ml 1N hydrochloric acid. Crystallization of this salt from 2-propanol-ethyl acetate gave the title compound, mp. 176°–179°. This material was identical to that prepared in Example 7C.

EXAMPLE 23

(A)

4-Amino-5-chloro-2-(cyclohexanon-2-yl)oxy-N-[2-(diethylamino)ethyl]benzamide

A mixture of 4-amino-5-chloro-N-[2-(diethylamino)ethyl]-2-hydroxybenzamide hydrochloride (15 g, 47 mmoles) (from Preparation 1A), tetrabutylammonium bromide (15 g, 47 mmoles), anhydrous potassium carbonate (34.32 g, 0.234 mole), 2-chlorocyclohexanone (8.9 g, 67 mmoles) in DMF (60 ml) was stirred for 4 days. The reaction mixture was partitioned between water and ethyl acetate. The ethyl acetate solution was washed with 0.4N NaOH, water and extracted with 1N HCl (50 ml). The acid extract was basified with saturated sodium carbonate solution and extracted with methylene chloride. The extract was dried and filtered through silica, the filtrate was concentrated and the concentrate diluted with pentane. The oiled-out material solidified on standing and was crystallized from toluene (30 ml) to yield the title compound, mp. 96°–99°.

Anal. Calc'd. for $C_{19}H_{28}ClN_3O_3$: C, 59.75; H, 7.39; N, 11.00; Cl, 9.29. Found: C, 59.65; H, 7.34; N, 10.68; Cl, 9.03.

(B)

4-Amino-5-chloro-2-(cyclohexanon-2-yl)oxy-N-[2-(diethylamino)ethyl]benzamide sulfate The 4-amino-5-chloro-2-(cyclohexanon-2-yl)oxy-N-[2-(diethylamino)ethyl]benzamide (190 mg, 0.5 mmole) was dissolved in 25 ml 2-propanol and treated with 1 ml of 1N sulfuric acid. The solution was concentrated under reduced pressure upon which crystallization occurred to yield the title compound, mp. 175° dec.

Anal Calc'd. for $C_{19}H_{30}ClN_3O_3S$: C, 47.54; H, 6.30; N, 8.75; Cl, 7.39; S, 6.68. Found: C, 47.52; H, 6.39; N, 8.46; Cl, 7.26; S, 6.80.

(C)

4-Amino-5-chloro-2-(cyclohexanon-2-yl)oxy-N-[2-(diethylamino)ethyl]benzamide hydrochloride was prepared, using 1N hydrochloric acid, in the same manner as the sulfate, mp. 150°–153° dec.

Anal. Calc'd. for $C_{19}H_{29}Cl_2N_3O_3$: C, 54.54; H, 6.99; N, 10.04. Found: C, 54.54; H, 7.03; N, 9.95.

EXAMPLE 24

4-Amino-5-chloro-N-[2-(diethylamino)ethyl]-2-(5-hexen-2-on-3-yl)oxybenzamide hydrochloride To a stirred suspension of sodium hydride (400 mg of 60%, 10 mmole, washed with n-pentane) in DMF (10 ml) was added 4-amino-5-chloro-N-[2-(diethylamino)ethyl]-2-(2-propanon-1-yl)oxybenzamide (3.4 g, 10 mmoles) (prepared in Example 5) under nitrogen. The mixture was stirred until evolution of hydrogen subsided. Allyl bromide (0.9 ml, 1.26 g, 10.5 mmoles) was added and stirring continued for 18 hours. The mixture was partitioned between water and methylene chloride and the organic phase washed with water, dried, concentrated and the residue chromatographed on deactivated silica using methylene chloride (100), methanol (4), ammonia (0.5) solvent system. The appropriate fractions were combined to give 1.14 g of free base. This was dissolved in 1-propanol and treated with 7 ml 2N HCl followed by concentration to give an oily residue. This was crystallized from acetoneether and the product recrystallized from 2-propanol to give 0.53 g of the title compound, mp. 171°–173°. The NMR spectrum (90 MHz) in $D_{20}$ gave the following resonances: δ7.88 (s, 1H); 6.42 (s, 1H); 6.12–4.88 (m, 3H); 3.76 (bd, 2H); 3.28 (m, 6H); 2.88 (bt, 2H); 2.4 (s, 3H); 1.35 (t, 6H).

Anal. Calc'd. for $C_{19}H_{29}Cl_2N_3O_3$: C, 54.55; H, 6.99; N, 10.04; Cl, 16.95. Found: C, 54.22; H, 7.11; N, 9.90; Cl, 16.51.

EXAMPLE 25

4-Amino-5-chloro-N-[2-(diethylamino)ethyl]-2-(pentan-2-on-3-yl)oxybenzamide

A solution of the tetrabutylammonium salt of 4-amino-5-chloro-N-[2-(diethylamino)ethyl]-2-hydroxybenzamide (10.5 g, 20 mmoles) (from Preparation No. 3) in acetonitrile (150 ml) was treated with 3-bromo-2-pentanone (3.3 g of 80%, 20 mmoles, contaminated with 15% of 1-bromo-2-pentanone) [obtained according to the procedure of E. T. Borrows, D. O. Holland and J. Kenyon, *J. Chem. Soc.* 1083, (1946)]. After 3 hours, the solvent was evaporated and the residue partitioned between ethyl acetate and water. The organic phase was washed with water, dried, and the solvent evaporated. The semisolid residue was triturated with ether to yield a solid which was recrystallized from etherpetroleum ether to yield 1.5 g of the title compound, mp. 75°–78°. The NMR spectrum (90 MHz) in $CDCl_3$ gave the following resonances: δ8.26 (s, 1H); 8.14 (bs, 1H); 6.1 (s, 1H); 4.5 (t, 1H); 4.4 (s, 2H); 3.69 (q, 2H); 2.64 (m, 6H); 2.1 (s, 3H); 2.1–1.7 (m, 2H); 1.05 (m, 9H).

Anal. Calc'd. for $C_{18}H_{28}ClN_3O_3$: C, 58.45; H, 7.63; N, 11.36; Cl, 9.59. Found: C, 58.30; H, 7.61; N, 11.20; Cl, 9.20.

EXAMPLE 26

4-Amino-2-(2-butanon-1-yl)oxy-5-chloro-N-[2-(diethylamino)ethyl]benzamide

A solution of the tetrabutylammonium salt of 4-amino-5-chloro-N-[2-(diethylamino)ethyl]-2-hydroxybenzamide (5.3 g, 10 mmoles) in acetonitrile (100 ml) was treated with 1-bromo-2-butanone (1.5 g, 10 mmoles) and stirred at 20° for 2 hours. The residue after concentration was treated with water and extracted with ethyl acetate and methylene chloride-2-propanol (5:1). The insoluble solid material was collected and combined with the organic extracts. Concentration of this mixture gave sticky crystalline material which was recrystallized from acetonitrile-water (4:1) to give the title product (3.1 g, 86%), mp. 103.0°–104.5°.

Anal. Calc'd. for $C_{17}H_{26}ClN_3O_3$: C, 57.37; H, 7.37; N, 11.81; Cl, 9.96. Found: C, 57.21; H, 7.34; N, 11.76; Cl, 9.67.

EXAMPLE 27

4-Amino-5-chloro-N-[2-(diethylamino)ethyl]-2-(pentan-2-on-1-yl)oxybenzamide

A solution of the tetrabutylammonium salt of 4-amino-5-chloro-N-[2-(diethylamino)ethyl]-2-hydroxybenzamide (1.54 g, 20 mmoles) in acetonitrile (150 ml) was treated with 1-bromo-2pentanone [3.3 g of 45% purity; obtained as a by-product in the bromination of 2-pentanone according to the procedure of E. T. Borrows, D. O. Holland and J. Kenyon, *J. Chem. Soc.* 1083 (1946) and identified by NMR], and left to stir for 16 hours. After evaporation of the solvent, the residue was partitioned between water and ethyl acetate. The organic phase was washed with water, dried, and the solvent evaporated. The residue was chromatographed over deactivated silica using methylene chloride (100), methanol (2), ammonia (0.5) solvent system. The appropriate fractions were combined to give a solid which was recrystallized from ethyl acetate to give 0.8 g of the title compound, mp. 112°–115°. The NMR spectrum (90 MHz) in CDCl$_3$ gave the following resonances: δ8.48 (bt, 1H); 8.24 (s, 1H); 6.14 (s, 1H); 4.7 (s, 2H); 4.4 (s, 2H); 3.56 (q, 2H); 2.66 (m, 8H); 1.7 (m, 2H); 1.06 (t, 9H).

Anal. Calc'd. for C18H2 C, 58.45; H, 7.63; N, 11.36. Found: C, 58.16; H, 7.66; N, 11.28.

EXAMPLE 28

4-Amino-5-chloro-2-(pentan-3-on-2-yl)oxy-N-(2-diethylaminoethyl)benzamide hydrochloride A mixture of 4-amino-5-chloro-N-[2-(diethylamino)ethyl]-2-hydroxybenzamide hydrochloride (4.83 g, 0.015 mmole) (from Preparation No. 1A), 2-bromo-3-pentanone (2.72 g, 0.0165 mmole) [prepared according to J. M. McIntosh and G. M. Masse, *J. Org. Chem.*, 40, 1294 (1975)] and potassium carbonate (4.14 g; 0.030 mmole) in 80 ml of dry DMF was stirred and heated at 90°–95° for 2 hours. The mixture was filtered and the DMF was removed under vacuum. The oily residue was redissolved in methylene chloride, washed sequentially with water, aqueous 1.0N NaOH and water and dried over Na$_2$SO$_4$. After evaporation of the solvent the crude oil was purified by flash chromatography on 86 g of silica gel (230–400 mesh) using a gradient elution of methanol-methylene chloride containing 0.25% NH$_{40}$H. The appropriate fractions were combined and evaporated to yield 4.31 g (77.7%) of light yellow gum.

The free base (4.30 g; 0.0116 mmole) was dissolved in 75 ml of isopropyl alcohol, 2.90 ml of aqueous 4.0N HCl was added, and the solution was concentrated to ca. 30 ml to give, after cooling, filtration and drying in vacuo 3.85 g (63.2%) of the crude product. This was recrystallized from acetonitrile to give the title compound as a white solid, mp. 100°–112°.

Anal. Calc'd. for C$_{18}$H$_{28}$ClN$_3$O$_3$HCl: C, 53.20; H, 7.19; N, 10.34; Cl, 17.45. Found: C, 53.24; H, 7.17; N, 10.26; Cl, 17.47.

EXAMPLE 29

4-Amino-5-chloro-N-[2-(diethylamino)ethyl]-2-[(3-methyl)-butan-2- on-1-yl]oxybenzamide A mixture of 4-amino-5-chloro-N-[2-(diethylamino)ethyl]-2-hydroxybenzamide hydrochloride (5.82 g, 18 mmoles), anhydrous potassium carbonate (12.48 g; 90 mmoles) in DMF (30 ml) and 1-bromo-3-methyl-2-butanone [4.5 g, 27 mmoles; prepared according to M. Gaudry and A. Marquet, *Org. Syn.* 55, 24 (1976)] was stirred for 20 hours under nitrogen. The mixture was poured into water (150 ml) and the solid collected, dried and crystallized from toluene to give the title compound (4.86 g, 73%), mp. 109°–110°. The NMR spectrum (90 MHz) gave the following resonances: δ8.56 (bt, 1H); 8.24 (s, 1H); 6.18 (s, 1H); 4.8 (s, 2H); 4.44 (s, 2H); 3.56 (m, 2H); 2.62 (m, 7H); 1.2 (d, 6H); 1.06 (t, 6H).

Anal. Calc'd. for C$_{18}$H$_{28}$ClN$_3$O$_3$: C, 58.45; H, 7.63; N, 11.36. Found: C, 58.38; H, 7.63; N, 11.25.

EXAMPLE 30

4-Amino-5-chloro-N-[2-(diethylamino)ethyl]-2-(3-phenyl-2- propanon-1-yl)oxybenzamide A solution of the tetrabutylammonium salt of 4-amino-5- chloro-N-[2-(diethylamino)ethyl]-2-hydroxybenzamide (3.45 g, 6.5 mmoles) and 1-chloro-3-phenyl-2-propanone (1.1 g, 6.5 mmoles) in acetonitrile was stirred for 18 hours at 20°. After removal of the acetonitrile at reduced pressure, the residue was treated with water and extracted with methylene chloride. The residue, after concentration of the extracts, was chromatographed on alumina (grade III) using ethyl acetate for elution. Combination of the appropriate fractions gave 1.1 g of product which was recrystallized from ethyl acetate to give the title compound, mp. 138°–139°.

Anal. Calc'd. for C$_{22}$H$_{28}$ClN$_3$O$_3$: C, 63.22; H, 6.71; N, 10.05; Cl, 8.48. Found: C, 63.23; H, 6.71; N, 9.92; Cl, 8.28.

EXAMPLE 31

4-Amino-5-chloro-N-[2-(diethylamino)ethyl]-2-[(3-methyl)butan-2-on-3-yl]oxybenzamide monohydrate A solution of the tetrabutylammonium salt of 4-amino-5-chloro-N-[2-(diethylamino)ethyl]-2-hydroxybenzamide (15.81 g, 30 mmoles) in DMF was treated with 3-bromo-3-methyl-2-butanone [4.95 g, 30 mmoles, (80% pure), prepared according to M. Gaudry and A. Marquet, *Tetrahedron* 26, 5611 (1970)]. After stirring for 20 hours, the solvent was evaporated and the residue was partitioned between ethyl acetate and water. The ethyl acetate layer was washed with 0.4N NaOH, H$_2$O, dried and the solvent evaporated. The residue was chromatographed over deactivated silica using methylene chloride (100), methanol (2), ammonia (0.5) solvent system. The appropriate fractions were combined to give 4.86 g of an oil. A portion of this (3.86 g) was crystallized from acetonitrile-water and recrystallized from methanol-water to give 1.23 g of title compound, mp. 84°–88°. The NMR spectrum (90 MHz) in CDCl$_3$ gave the following resonances: δ 8.24 (s, 1H); 8.08 (bs, 1H); 5.92 (s, 1H); 4.34 (s, 2H); 3.58 (q, 2H); 2.6 (q, 6H); 2.32 (s, 3H); 1.66 (s, 2H); 1.64 (s, 6H); 1.04 (t, 6H).

Anal. Calc'd. for C$_{18}$H$_{28}$ClN$_3$O$_3$.H$_2$O: C, 55.73; H, 7.80; N, 10.83; Cl, 9.14; H$_2$O, 4.67. Found: C, 55.75; H, 7.83; N, 10.72; Cl, 8.74; H$_2$O, 4.62.

EXAMPLE 32

4-Amino-2-(2-butanon-3-yl)oxy-5-chloro-N-[2-(dimethylamino)ethyl]benzamide

A solution of 4-amino-5-chloro-N-[2-(dimethylamino)ethyl]-2-hydroxybenzamide (1.90 g, 7.37 mmoles) (prepared in Example 17), potassium carbonate (3.06 g, 2.21 mmoles), sodium iodide (1.11 g, 7.37 mmoles) and 91% 3-bromo-2-butanone (1.81 g, 12 mmoles) in DMF (30 ml) was stirred for 1.5 hours. The solvent was removed in vacuo and the residue partitioned between water and methylene chloride. The aqueous phase was extracted two more times with methylene chloride. The combined extracts were dried and concentrated in vacuo. The residue was chromatographed on a silica gel column using the solvent system of methylene chloride (99.5)-methanol (0.5)-ammonia (0.2). The appropriate fractions were combined and concentrated in vacuo to give a solid. This was recrystallized from acetonitrile to give 1.85 g of the title compound as a colorless solid, mp. 124°–125°.

Anal. Calc'd for $C_{15}H_{22}ClN_3O_3$: C, 54.96; H, 6.76; N, 12.82; Cl, 10.82. Found: C, 55.17; H, 6.86; N, 12.80; Cl, 10.83.

EXAMPLE 33

4-Amino-5-chloro-N-[2-(diethylamino)ethyl]-2-[2-(2-hydroxy-3-phenylpropyl)]oxybenzamide A solution of the tetrabutylammonium salt of 4-amino-5-chloro-N-[2-(diethylamino)ethyl]-2-hydroxybenzamide (2.64 g, 5 mmoles) and 1-chloro-2-hydroxy-3-phenylpropane (0.85 g, 5 mmoles) in 10 ml of DMF was heated at reflux for 2 hours. The mixture was concentrated at reduced pressure. The residue was taken up in methylene chloride, washed with dilute sodium hydroxide, dried over $Na_2SO_4$ and concentrated. The product was recrystallized from ethyl acetate to give the title compound (1.05 g), mp. 155°–157°.

Anal. Calc'd for $C_{22}H_{30}ClN_3O_3$: C, 62.92; H, 7.20; N, 10.01; Cl, 8.44. Found: C, 62.71; H, 7.26; N, 10.01; Cl, 8.27.

EXAMPLE 34

4-Amino-5-chloro-N-[2-(diethylamino)ethyl]-2-(2-hydroxyiminobut-3-yl)oxybenzamide A solution of 4-amino-2-(2-butanon-3-yl)oxy-5-chloro-N[2-diethylamino)ethyl]benzamide hydrochloride (1.14 g, 2.9 mmoles) (prepared in Example 7C) and hydroxylamine hydrochloride (0.3 g, 4.3 mmoles) in methanol (20 ml) was refluxed for 15 minutes. The solvent was evaporated and the residue was partitioned between methylene chloride and a saturated solution of sodium carbonate. The organic phase was washed with water, dried and the solvent evaporated. The residue was crystallized from ethyl acetate and petroleum ether to yield the title compound, mp. 113°–115° (0.37 g). The NMR spectrum (90 MHz) in $CDCl_3$ gave the following resonances: δ9.8 (bs, 1H); 8.16 (s, 1H); 6.4 (s, 1H); 4.96 (q, 1H); 4.4 (s, 2H); 4.02–3.08 (bm, 3H); 2.66 (m, 6H); 1.84 (s, 3H); 1.6 (d, 3H); 1.08 (t, 6H).

Anal. Calc'd for $C_{17}H_{27}ClN_4O_3$: C, 55.05; H, 7.34; N, 15.11; Cl, 9.56. Found: C, 54.91; H, 7.34; N, 14.97; Cl, 9.45.

EXAMPLE 35

α-{3-Amino-4-chloro-6-[N-(2-[diethylamino]ethyl)]carbamoylphenoxy}phenylacetic acid, ethyl ester To a well-stirred suspension of sodium hydride (0.36 g of 60%, 9 mmoles, washed with n-pentane) in 5 ml of dry DMF was added a solution of 4-amino-5-chloro-N-[2-(diethylamino)ethyl]2-hydroxybenzamide (2.28 g, 8 mmoles) (from Preparation No. 1B) in 10 ml of dry DMF. After evolution of hydrogen had ceased, to this was added dropwise a solution of ethyl α-bromophenyl acetate (2.12 g, 8.7 mmoles) in 5 ml of dry DMF. After an additional 18 hours at ambient temperature, the mixture was concentrated in vacuo and the residue partitioned between water (200 ml) and methylene chloride (75 ml). The aqueous phase was extracted twice with 75 ml portions of methylene chloride. After combining, the organic phase was washed three times with 50 ml of 10% aqueous sodium hydroxide and three times with brine; dried over sodium sulfate, filtered, concentrated in vacuo, to give 3.5 g of oil which slowly crystallized. Trituration with pentane gave 3.34 g of the title compound, mp. 84°–87° C. The NMR spectrum (90 MHz) in $CDCl_3$ gave the following resonances: δ8.55 (bt, 1H); 8.20 (s, 1H); 7.50 (m, 5H); 6.09 (s, 1H); 5.65 (s, 1H); 4.25 (m, 4H); 3.55 (m, 2H); 2.60 (m, 6H); 1.05 (m, 9H).

Anal. Calc'd. for $C_{23}H_{30}ClN_3O_4$: C, 61.66; H, 6.76; N, 9.38. Found: C, 61.75; H, 6.76; N, 9.27.

EXAMPLE 36

4-Amino-5-chloro-N-[2-(diethylamino)ethyl]-2-(2-hydrazino-2oxoethoxy)benzamide Trihydrate A suspension of 4-amino-5-chloro-N-[2-(diethylamino)ethyl]-2-(2-methoxy-2-oxoethoxy)benzamide (3.58 g, 10 mmoles) (prepared in Example 15) in 64% hydrazine hydrate in water (0.6 g, 12 mmoles) and methanol (3 ml) was stirred for 1 hour, when a clear solution was formed. The mixture was concentrated in vacuo and the residue recrystallized from water, to give, after drying, 3.65 g (88.6%) of the title compound as the trihydrate, mp. 130°–131° C.

Anal. Calc'd. for $C_{15}H_{24}N_5ClO_3 \cdot 3H_2O$: C, 43.73; H, 7.34; N, 17.00; Cl, 8.60; $H_2O$, 13.12. Found: C, 44.07; H, 7.46; N, 17.19; Cl, 8.77; $H_2O$, 11.60.

EXAMPLE 37

4-Amino-5-chloro-N-[2-(diethylamino)ethyl]-2-[2-(2-acetylhydrazino)-2-oxoethoxy]benzamide Acetate 4-Amino-5-chloro-N-[2-(diethylamino)ethyl]-2-(2-hydrazino-2-oxoethoxy)benzamide trihydrate (1.0 g, 2.43 mmoles) (prepared in Example 36) was dried at 110° C./0.02 mm for 3 hours to give the corresponding anhydrous material (865 mg). This was treated with a solution of acetic anhydride (248 mg, 2.428 mmoles) in methylene chloride (5 ml) until clear solution was formed. The solution was concentrated in vacuo to give 1.115 g (100%) of the title compound as white hygroscopic solid.

Anal. Calc'd. for $C_{19}H_{30}N_5ClO_6$: C, 49.62; H, 6.58; N, 15.23; Cl, 7.71. Found: C, 48.86; H, 6.67; N, 14.87; Cl, 8.20.

EXAMPLE 38

4-Amino-5-chloro-N-[2-(diethylamino)ethyl]-2-[3-(phthalimido)propoxy]benzamide

To a suspension of the tetra-n-butylammonium salt of 4-amino-5-chloro-N-[2-(diethylamino)ethyl]-2-hydroxybenzamide (15.8 g, 30 mmoles) (prepared in Preparation 3) in acetonitrile (50 ml) was added N-(3-bromopropyl)phthalimide and the mixture stirred for 16 hours at ambient temperature and 1 hour at 65°–70° C. This was concentrated in vacuo and the residue partitioned between water and a 1:1 mixture of ether and methylene chloride. The organic phase was washed several times with water, dried and concentrated to small volume causing crystallization. This was filtered and the solid washed with ether to give 12.3 g (86.7%) of the title product as white solid, mp. 141°–143°.

Anal. Calc'd. for $C_{24}H_{29}N_4ClO_4$: C, 60.94; H, 6.18; N, 11.85; Cl, 7.5. Found: C, 61.05; H, 6.43; N, 11.80; Cl, 7.63.

EXAMPLE 39

4-Amino-2-(3-aminopropoxy)-5-chloro-N-[2-(diethylamino)ethyl]- benzamide

A mixture of 4-amino-5-chloro-N-[2-(diethylamino)ethyl]-2-[3-(phthalimide)propoxy]benzamide (4.73 g, 10 mmoles) (prepared in Example 38), 64% hydrazine hydrate (800 mg, 16 mmoles) and absolute ethanol (15 ml) was heated briefly to reflux until clear solution was formed. The solution was heated 16 hours at 55°–57° C. and then 2 hours at reflux. After cooling, a solid was filtered off and washed with ethanol. The combined filtrate and washings were concentrated in vacuo. The residue was dissolved in methylene chloride, and insoluble solid removed by filtration. The filtrate was washed with water, dried and concentrated in vacuo to give a solid product. This was recrystallized from methylene chloride-n-pentane to give 2.96 g (86.3%) of the title compound as white solid, mp 119°–121° C.

Anal. Calc'd. for $C_{16}H_{27}N_4ClO_2$: C, 56.05; H, 7.94; N, 16.34; Cl, 10.34. Found: C, 56.05; H, 7.92; N, 16.10; Cl, 10.47.

EXAMPLE 40

4-Amino-5-chloro-N-[2-(diethylamino)ethyl]-2-[2-(methylamino) 2-oxoethoxy]benzamide To a suspension of 4-amino-5-chloro-N-[2-(diethylamino)ethyl]-2-(2-methoxy-2-oxoethoxy)benzamide (1.074 g, 3 mmoles) (prepared in Example 15), in a 1N solution of methylamine in toluene (10 ml) was added 3 ml of methanol and the mixture stirred for 16 hours. This was concentrated in vacuo and the residue crystallized from methanol-ether to give 815 mg (76%) of the title compound as white solid; mp. 149°–151° C.

Anal. Calc'd. for $C_{16}H_{25}N_4ClO_3$: C, 53.85; H, 7.06; N, 15.70; Cl, 9.94. Found: C, 53.85; H, 7.16; N, 15.63; Cl, 10.00.

EXAMPLE 41

4-Amino-5-chloro-N-[2-(diethylamino)ethyl]-2-[(2-hydroxy)but-3-yl]oxybenzamide (mixture of threo and erythro isomers)

A mixture of 4-amino-2-(2-butanon-3-yl)oxy-5-chloro-N-[2-(diethylamino)ethyl]benzamide (obtained by treating 1.2 g, 3.1 mmoles, of the corresponding hydrochloride salt, prepared in Example 7C, with saturated sodium carbonate solution) and sodium borohydride (100 mg) in ethanol (20 ml) was heated under reflux for one hour. The solution was concentrated, diluted with water, acidified with 2N hydrochloric acid, and basified with saturated sodium carbonate solution. The mixture was extracted with methylene chloride to yield 1.16 g of foam. This material was chromatographed over deactivated silica using methylene chloride (100), methanol (2), ammonia (0.5) as the solvent system. The appropriate fractions were combined to yield the title compound (470 mg) as a foamy mixture of diastereoisomers. The NMR spectrum (90 MHz) in CDCl$_3$ gave the following resonances: δ 8.54 (bd, 1H); 8.2, 8.15 (2s, 1H); 6.32, 6.35 (2s, 1H); 4.36 (s, 2H); 4.24–4 (m, 1H); 4–2.12 (m, 3H); 2.8–2.52 (m, 6H); 1.41–0.96 (m, 12H).

Anal. Calc'd. for $C_{17}H_{28}ClN_3O_3$: C, 57.05; H, 7.89; N, 11.74; Cl, 9.91. Found: C, 56.34; H, 7.79; N, 11.55; Cl, 9.65.

EXAMPLE 42

4-Amino-5-chloro-N-[2-(diethylamino)ethyl]-2-(ethyl-3-methoxycroton-4-yl)oxybenzamide The general procedure of Example 35 was repeated except that the ethyl α-bromophenylacetate utilized therein was replaced by an equimolar amount of ethyl 3-methoxy-4-chlorocarbonate (prepared according to U.S. Pat. No. 4,348,333). The solvent (DMF) was removed in vacuo, the residue treated with water and methylene chloride. The latter was washed with 10% sodium hydroxide, water and brine followed by drying over sodium sulfate, filtration and concentration. The crude solid was recrystallized from ether/methylene chloride giving the title compound, mp. 109°–111° C.

Anal. Calc'd. for $C_{20}H_{30}ClN_3O_5$: C, 55.99; H, 7.06; N, 9.80. Found: C, 55.96; H, 7.14; N, 9.77.

EXAMPLE 43

4-Amino-5-chloro-N-[2-(diethylamino)ethyl]-2-(1,3-dioxolan-2-yl)oxybenzamide

The general procedure of Example 35 was repeated except that the ethyl α-bromophenylacetate utilized therein was replaced by an equimolar amount of 2-bromoethyl-1,3-dioxalane and the reaction mixture heated to 80° C. for 30.5 hours. The solvent (DMF) was removed in vacuo, the residue treated with brine and methylene chloride; the latter washed with 10% sodium hydroxide and brine, dried over sodium sulfate, filtered and concentrated. Recrystallization from methylene chloride/hexane provided the title compound, mp. 93°–95° C.

Anal. Calc'd. for $C_{17}H_{26}ClN_3O_4$: C, 54.90; H, 7.06; N, 11.30. Found: C, 54.98; H, 7.07; N, 11.40.

EXAMPLE 44

4-Amino-5-chloro-N-[2-(diethylamino)ethyl]-2-(oxazolidin)-2-one-5-ylmethyl)oxybenzamide Fumarate Equimolar amounts (6 mmoles) of the tetra-n-butylammonium salt of 4-amino-5-chloro-N-[2-(diethylamino)ethyl]-2-hydroxybenzamide (prepared in Preparation 3) and 5-chloromethyl-2-oxazolidinone in 15 ml DMF were heated at reflux with stirring for 3 hours. After remova of the solvent the residue was dissolved in methylene chloride and washed with water. After drying over MgSO$_4$ and concentration, 2.7 g of crude product was obtained. This material was purified by chromatography on alumina grade III using ethyl acetate containing 5 and 10% ethanol as eluant. The partially purified product (1.1 g) in 1-propanol was treated with fumaric acid (0.33 g) to give 0.81 g (30.5%) of the crystalline fumarate salt, mp. 165°–167° C.

Anal. Calc'd. for $[C_{17}H_{25}ClN_4O_4]_2 \cdot C_4H_4O_4$: C, b 51.52; H, 6.15; N, 12.65; Cl, 8.01. Found: C, 51.21; H, 6.18; N, 12.40; Cl, 7.99.

EXAMPLE 45

4-Amino-5-chloro-N-[2-(diethylamino)ethyl]-2-(2-pyridinomethyl)oxybenzamide

To a solution of the tetra-n-butylammonium salt of 4-amino-5-chloro-N-[2-(diethylamino)ethyl]-2-hydroxybenzamide (2.64 g, 0.005 mole) (prepared in Preparation 3) in 30 ml acetonitrile was added 2-chloromethylpyridine (prepared by K$_2$CO$_3$ neutralization of 0.01 mole of the corresponding hydrochloride). The resultant reaction mixture was stirred for 18 hours and then concentrated. The residue was chromatographed on alumina grade III using ethyl acetate and ethyl acetate, ethanol (100:2) as eluants to give 1.8 g of purified product which was recrystallized from 2:1 ethyl acetate-n-hexane. There was obtained 1.45 g (77%) of the title compound, mp. 84°–85° C.

Anal. Calc'd. for $C_{19}H_{25}ClN_4O_2$: C, 60.55; H, 6.69; N, 14.87; Cl, 9.41. Found: C, 60.62; H, 6.76; N, 14.81; Cl, 9.34.

EXAMPLE 46

4-Amino-5-chloro-N-[2-(diethylamino)ethyl]-2-(2-methoxyethoxyethyl)oxybenzamide

The general procedure of Example 35 was repeated except that the ethyl α-bromophenylacetate utilized therein was replaced by an equimolar amount of 1-bromo-2-(2-methoxyethoxy)ethane. The solvent (DMF) was removed in vacuo, the residue treated with brine and methylene chloride; the latter washed with 10% sodium hydroxide and brine, dried over sodium sulfate, filtered and concentrated. Recrystallization from ether provided the title compound, mp. 49°–51° C.

Anal. Calc'd. for $C_{18}H_{30}ClN_3O_4$: C, 55.72; H, 7.81; N, 10.83. Found: C, 55.50; H, 7.69; N, 10.78.

EXAMPLE 47

4-Amino-2-(2-aminoethoxy)-5-chloro-N-[2-(diethylamino)ethyl]benzamide

To a suspension of one teaspoonful of Raney nickel (well washed with methanol) in methanol (130 ml) was added 4-amino-5-chloro-2-cyanomethyl-N-[2-(diethylamino)ethyl]benzamide (12.05 g, 37.1 mmoles) (prepared in Example 13), and the mixture hydrogenated at 40 psi for 5 hours. The catalyst was removed by filtration under nitrogen and the filtrate concentrated in vacuo. This was dissolved in methylene chloride and washed with 1N sodium hydroxide (4×25 ml). The washings were back extracted with methylene chloride and the organic phases combined, dried and concentrated in vacuo to give 5.56 g of the title product as a semi-solid. This was recrystallized from methanol-ether in the cold to give a sample, mp. 97°–99° C.

Anal. Calc'd. for $C_{15}H_{25}ClN_4O_2$: C, 54.78; H, 7.60; Cl, 10.78; N, 17.04. Found: C, 54.71; H, 7.64; Cl, 10.91; N, 16.81.

EXAMPLE 48

2-(2-Acetylaminoethoxy)-4-amino-5-chloro-N-[2-(diethylamino)ethyl]benzamide

To a solution of 4-amino-2-(2-aminoethoxy)-5-chloro-N-[2-(diethylamino)ethyl]benzamide (780 mg, 2.4 mmoles) (prepared in Example 47) in methylene chloride was added acetic anhydride (245 mg, 2.4 mmoles) and the mixture stirred for 30 minutes. This was concentrated in vacuo and the residue was partitioned between methylene chloride and sodium bicarbonate solution. The organic phase was concentrated and the residue flash-chromatographed on silica using methylene chloride:methanol:ammonia (100:4:0.5) solvent system. The appropriate fractions were combined and concentrated in vacuo. The residue was recrystallized from methylene chloride-ether to give 445 mg of the title compound as a white solid, mp. 143°–145° C.

Anal. Calc3 d. for $C_{17}H_{27}ClN_4O_3$: C, 55.05; H, 7.37; Cl, 9.56; N, 15.11. Found: C, 54.82; H, 7.28; Cl, 9.71; N, 14.54.

EXAMPLE 49

4-Amino-5-chloro-N-[2-(diethylamino)ethyl]-2-[3-(methylthio)propoxy]benzamide

To a solution of tetrabutylammonium salt of 4-amino-5-chloro-N-[2-(diethylamino)ethyl]-2-hydroxybenzamide (10.54 g, 20 mmoles) (prepared in Preparation No. 3) in DMF (100 ml) was added 1-bromo-3-chloropropane (3.268 g, 2.2 ml, 20.76 mmoles) and the mixture stirred for 2 hours at ambient temperature and another 30 minutes at 40° C. The mixture was cooled to 0° C and poured over sodium hydride (1.0 g of 60% mineral oil dispersion, 25 mmoles, washed with n-pentane) under nitrogen. The mixture was stirred in the cold while methyl mercaptan gas was bubbled in until evolution of hydrogen ceased. The mixture was heated at 35°–40° C. for 2 hours, poured into water (700 ml) and after standing for 1 hour the resultant solid was isolated by suction to give after drying in air 7.06 g (94%) of crude product, mp. 58°–59° C. This was dissolved in methylene chloride and filtered over a short column packed with silica and alumina. The filtrate was concentrated and the residue crystallized from ether to give 4.95 g (66%) of the title compound as a white solid, mp. 79°–80° C.

Anal. Calc'd. for $C_{17}H_{28}ClN_3O_2S$: C, 54.61; H, 7.55; Cl, 9.48; N, 11.24; S, 8.56. Found: C, 54.56; H, 7.52; Cl, 9.38; N, 11.10; S, 8.23.

EXAMPLE 50

4-Amino-5-chloro-N-[2-(diethylamino)ethyl]-2-[3-(methylsulfinyl)propoxy]benzamide To a stirred solution of product from Example 49 (1.496 g, 4 mmoles) in 2N hydrochloric acid (5.0 ml, 10 mmoles) and water (20 ml) was added sodium periodate (856 mg, 4.0 mmoles) and the mixture stirred for 2.5 hours. It was then basified with 4N sodium hydroxide (3 ml) and extracted with methylene chloride (3×30 ml). The extract was concentrated in vacuo and the residue flash-chromatographed on deactivated silica column using methylene chloride:methanol:ammonia (100:3.5:0.5) solvent system. The appropriate fractions were combined and concentrated to give a yellow oil which crystallized from methylene chloride-ether to give 770 mg of the title product as a light yellow solid, mp. 116°–117° C.

Anal. Calc'd. for $C_{17}H_{28}ClN_3O_3S$: C, 52.37; H, 7.24; Cl, 9.09; N, 10.78; S, 8.21. Found: C, 52.31; H, 7.25; Cl, 8.70; N, 10.68; S, 7.88.

EXAMPLE 51

4-Amino-5-chloro-N-[2-(diethylamino)ethyl]-2-(1H-4,5-dihydroimidazol-2-yl)methoxybenzamide A mixture of 4-amino-5-chloro-2-cyanomethoxy-N-[2-(diethylamino)ethyl]benzamide (3.25 g, 10 mmoles) (prepared in Example 13) and 1,2-diaminoethane (0.6 g, 10 mmoles) in methanol (25 ml) was heated at reflux for 3 hours. The reaction mixture was concentrated to leave a crystalline residue which was recrystallized from ethyl acetate to give the title product (2.78 g, 76%), mp. 144°–145° C.

Anal. Calc'd. for $C_{17}H_{26}ClN_5O_2$: C, 55.50; H, 7.12; Cl, 9.64; N, 19.04. Found: C, 55.64; H, 7.21; Cl, 9.75; N, 18.94.

EXAMPLE 52

4-Amino-5-chloro-N-[2-(diethylamino)ethyl]-2-(2-thienoylmethoxy)benzamide

A mixture of 2-thiophenecarboxylic acid (2.6 g, 20 mmoles), thionyl chloride (2.4 g, 20 mmoles) and toluene (15 ml) was heated at reflux for one hour. The reaction was concentrated to leave an oil (2.8 g). A solution of this oil in diethyl ether (10 ml) was added to a solution of diazomethane (prepared from 8.1 g, 80 mmoles, of N-methyl-N-nitrosourea) in ether (200 ml). After stirring for 2 hours at 20° C., the reaction was treated with hydrogen chloride gas (excess) over a period of 20 minutes. After stirring for an additional ½ hour, the reaction mixture was concentrated to give chloroacetyl-2-thiophene as a dark oil (3.2 g). A portion of this dark oil (1.6 g) was taken up in acetonitrile (25 ml), treated with the tetra-n-butylammonium salt of 4-amino-5-chloro-N-[2-(diethylamino)ethyl]-2-hydroxybenzamide (2.6 g, 5 mmoles) (prepared in Preparation No. 3) and stirred for 18 hours. After concentration, the residue was purified by chromatography on alumina (grade III) using ethyl acetate containing 2% ethanol for elution, to give the title product, which was recrystallized from acetonitrile, mp. 135°–139° C.

Anal. Calc'd. for $C_{19}H_{24}ClN_3O_2S$: C, 55.67; H, 5.90; N, 10.25; S, 7.82. Found: C, 55.86; H, 5.91; N, 10.18; S, 7.54.

EXAMPLE 53

4-Amino-5-chloro-2-(2-chloroethoxy)-N-[2-(2-diethylamino)ethyl]benzamide

To a stirred solution of sodium salt of 4-amino-5-chloro-N-[2-(diethylamino)ethyl]-2-hydroxybenzamide prepared from the corresponding hydrochloride salt (5.0 g, 16 mmoles) (prepared in Preparation No. 1) and sodium hydride (1.3 g of 60%, 32.6 mmoles) in 15 ml DMF was added 2-chloroethyl-p-toluenesulfonate (3.64 g, 16 mmoles), and the mixture was stirred for 16 hours at ambient temperature and another 3 hours at 80°–90° C. The mixture was concentrated in vacuo and the residue partitioned between brine and methylene chloride. The organic phase was washed with aqueous sodium hydroxide, brine, water, dried and concentrated in vacuo. The residue was recrystallized from ether to give 2.02 g of the title compound, mp. 153°–154° C.

Anal. Calc'd. for $C_{15}H_{23}Cl_2N_3O_2$: C, 51.72; H, 6.67; N, 12.06. Found: C, 51.76; H, 6.64; N, 11.42.

EXAMPLE 54

4-Amino-5-chloro-N-[2-(diethylamino)ethyl]-2-[2-methyl-2-(1,3-dioxolan)-4-yl]oxybenzamide To a well-stirred suspension of pentane-washed sodium hydride (1.26 g of 60%, 32 mmoles) in 3 ml of dry DMF was added 4-amino-5-chloro-N-[2-(diethylamino)ethyl]-2-hydroxybenzamide (8.57 g, 3 mmoles) in 12 ml DMF over 35 minutes. After stirring for one and one-half hours, 2-methyl-2-(2-iodoethyl)-1,3dioxolone (6.54 g, 27 mmole) [prepared according to *J. Org. Chem.*, 48, 5381–5382 (1983)] was added over 8 minutes followed by stirring for 24 hours. The mixture was then poured into 300 ml of brine followed by extraction with four 100 ml portions of methylene chloride. After combining, the organic phase was washed twice with 100 ml of 10% aqueous sodium hydroxide and brine; dried over sodium sulfate, and concentrated in vacuo to give 9.44 g of oil. A 5 g aliquot of this material was purified by flash chromatography on a silica gel column eluted with a solvent mixture composed of methylene chloride (93), methanol (7), ammonia (0.2). Appropriate fractions were combined, and concentrated in vacuo to give 2.68 g of the title compound, mp. 84°–86° C.

Anal. Calc'd. for $C_{19}H_{30}ClN_3O_4$: C, 57.05; H, 7.58; N, 10.51. Found: C, 56.82; H, 7.55; N, 10.40.

EXAMPLE 55

4-Amino-5-chloro-2-[2-(dimethylamino)-2-oxoethoxy]-N-[2-diethylamino)ethyl]benzamide The general procedure of Example 40 was repeated except that the methylamine utilized therein was replaced by dimethylamine. After reacting for 6 days the mixture was concentrated in vacuo and the residue partitioned between water and methylene chloride. The organic phase was dried, concentrated in vacuo, and the residue crystallized from methanol-methylene chlorideether to give the title compound as a white solid containing one-half mole of water of crystallization, mp. 130°–131° C.

Anal. Calc'd. for $C_{17}H_{27}ClN_4O_3 \cdot \frac{1}{2}H_2O$: C, 53.74; H, 7.42; Cl, 9.33; N, 14.36. Found: C, 54.09; H, 7.17; Cl, 9.02; N, 14.74.

EXAMPLE 56

4-Amino-5-chloro-N-[2-(diethylamino)ethyl]-2-(4-diethylamino-4-oxobutoxy)benzamide To a well-stirred suspension of pentane-washed sodium hydride (0.52 g of 60%, 3 mmole) in 3 ml dry DMF was added 4-amino-5-chloro-N-[2-(diethylamino)ethyl]-2-hydroxybenzamide (3.43 g, 12 mmoles) (prepared as in Example 53). To this was added 10 ml of DMF and the mixture was stirred at ambient temperature for 45 minutes then warmed to about 50° C. for 15 minutes whereupon 4-chloro-N,N-diethylbutyramide (1.92 g, 11 mmoles) was added. The mixture was then stirred at 60°–70° C. for 6 hours, at room temperature for 2 days and then at 60-70° C. for a further 4 hours. After cooling, the mixture was poured into 400 ml of brine and extracted with methylene chloride (4×100 ml). After combining, the organic phase was washed two times with 100 ml of 10% aqueous sodium hydroxide and brine, dried over sodium sulfate, filtered and concentrated in vacuo to give an oil (3.75 g). This was purified by flash chromatography on silica gel to give 1.64 g of the title compound as an oil.

Anal. Calc'd. for $C_{21}H_{35}ClN_4O_3$: C, 59.06; H, 8.28; N, 13.12. Found: C, 57.71; H, 8.15; N, 12.7.

EXAMPLE 57

2-(2-Acetoxyethoxy)-4-amino-5-chloro-N-[2-(diethylamino)ethyl]benzamide

A solution of the tetrabutylammonium salt of 4-amino-5-chloro-N-[2-(diethylamino)ethyl]-2-hydroxybenzamide (5.27 g, 10 mmoles) (prepared in Preparation No. 3) in acetonitrile (100 ml) and 2-bromoethylacetate (2 g, 12 mmoles) was stirred for 48 hours. The solvent was evaporated and the residue partitioned between ethyl acetate and water. The organic layer was washed with ice-cold 0.4N sodium hydroxide solution, water, dried and the solvent evaporated. The residue was chromatographed over deactivated silica using methylene chloride (100), methanol (2), ammonia (0.5) solvent system. The appropriate fractions were combined and the solvent evaporated to leave a residue of 3.18 g (85%) of the title compound. Crystallization from toluene gave a sample, mp. 101°–102° C.

Anal. Calc'd. for $C_{17}H_{26}ClN_3O_4$: C, 54.91; H, 7.05; N, 11.30. Found: C, 54.86; H, 7.01; N, 11.28.

EXAMPLE 58

4-Amino-5-chloro-N-[2-diethylamino)ethyl]-2-[4-(methylsulfinyl)butoxy]benzamide (A)

4-Amino-5-chloro-N-[2-(diethylamino)ethyl]-2-[4-(methylthio)butoxy]benzamide

A mixture of tetrabutylammonium salt of 4-amino-5-chloro-N-[2-(diethylamino)ethyl]-2-hydroxybenzamide (15.82 g, 30 mmoles) (prepared in Preparation No. 3) in DMF (150 ml) and 1,4-dibromobutane (6.48 g, 30 mmoles) was stirred for 24 hours. The solution was chilled and poured into a 500 ml flask containing sodium hydride (1.5 g, 37.5 mmoles, of a 60% emulsion washed with pentane). The suspension was cooled in ice, stirred and methyl mercaptan was passed into the mixture until the evolution of hydrogen ceased. The clear solution was heated at 35°–50° C. for 5 hours, poured into 1400 ml of water and extracted with ethyl acetate. The organic layer was washed with water, dried, and the solvent evaporated. The residue was chromatographed over deactivated silica, using methylene chloride (100), methanol (2), ammonia (0.5) solvent system. Two compounds were obtained: (1) 1,4-bis{4-amino-5-chloro-N-[2-(diethylamino)-ethyl]-2-oxybenzamide}butane, mp. 172°–176° C. and (2) the title compound, 2.5 g crystallized from 2-propanol, mp. 101°–103° C.

Anal. Calc'd. for $C_{18}H_{30}ClN_3O_2S$: C, 55.72; H, 7.79; N, 10.83; Cl, 9.14; S, 8.27. Found: C, 55.59; H, 7.87; N, 10.81; Cl, 9.26; S, 8.19.

(B)

4-Amino-5-chloro-N-[2-(diethylamino)ethyl]-2-[4-methylsulfinyl)butoxy]benzamide

The general procedure from Exampe 21 is repeated except that the 4-amino-5-chloro-N-[2-(diethylamino)ethyl]-2[2-(methylthio)ethoxy]benzamide utilized therein was replaced with the product from Step A to give the title compound in 78% yield after chromatography on silica and crystallization from methylene chloride-ether, as a solid, mp. 80°–83° C.

Anal. Calc'd. for $C_{18}H_{30}ClN_3O_3S$: C, 53.51; H, 7.49; N, 10.40; Cl, 8.78; S, 7.94. Found: C, 53.70; H, 7.72; N, 10.36; Cl, 8.40; S, 7.78.

EXAMPLE 59

4-Amino-5-chloro-N-[2-(diethylamino)ethyl]-2-[2-(1-pyrrolidinyl) 2-oxoethoxy]benzamide A solution of 4-amino-5-chloro-N-[2-(diethylamino)ethyl]-2-(2-methoxy-2-oxoethoxy)benzamide (1.07 g, 3 mmoles) (prepared in Example 15) in methanol (10 ml) and pyrrolidine (0.952 g, 23 mmoles) was refluxed overnight. The solvent was evaporated and the residue was chromatographed over deactivated silica using methylene chloride (100), methanol (2.5), ammonia (0.5) solvent system. The appropriate fractions were combined, the solvent evaporated and the residue crystallized from 2-propanol and recrystallized from methanol-ether to yield 0.86 g (72%) of the title compound, mp. 160°–162° C.

Anal. Calc'd. for $C_{19}H_{29}ClN_4O_3.\frac{1}{4}H_2O$: C, 56.84; H, 7.40; N, 13.96. Found: C, 56.89; H, 7.24; N, 13.67.

EXAMPLE 60

4-Amino-5-chloro-N-[2-(diethylamino)ethyl]-2-[2-(ethylsulfinyl)ethoxy]benzamide (A)

4-Amino-5-chloro-N-[2-(diethylamino)ethyl]-2-[2-ethylthio)ethoxy]benzamide

The general procedure of Example 20 was repeated except that the 2-chloroethyl methyl sulfide utilized therein was replaced with 2-chloroethyl ethyl sulfide to give the title compound as an off-white solid from acetonitrile, mp. 92°–94° C., in 61% yield.

Anal. Calc'd. for $C_{17}H_{28}ClN_3O_2S$: C, 54.60; H, 7.55; N, 11.24; Cl, 9.48; S, 8.58. Found: C, 54.14; H, 7.57; N, 10.97; Cl, 9.03; S, 8.58.

(B)

4-Amino-5-chloro-N-[2-(diethylamino)ethyl]-2-[2-(ethylsulfinyl)ethoxy]benzamide

Substitution of the product from Step A in the procedure of Example 21 gave the title compound in 53% yield as light yellow, shiny crystals, mp. 140°–142° C. after recrystallization from acetonitrile.

Anal. Calc'd. for $C_{17}H_{28}ClN_3O_3S$: C, 52.36; H, 7.24; N, 10.78; Cl, 9.09; S, 8.22. Found: C, 52.56; H, 7.38; N, 10.75; Cl, 8.89; S, 8.21.

EXAMPLE 61

Cis-4-amino-5-chloro-N-{1-[3-(4-fluorophenoxy)-propyl]-3-methoxy4-piperidinyl}-2-[2-(methylthio)ethoxy]benzamide monohydrate (A)

Cis-4-amino-5-chloro-N-{1-[3-(4-fluorophenoxy)-propyl]-3-methoxy-4-piperidinyl}-2-hydroxybenzamide The general procedure of Preparation No. 1 was repeated except that the 4-amino-5-chloro-N-[2-(diethylamino)ethyl]-2-methoxybenzamide utilized therein was replaced by cis-4-amino-5-chloro-N-{1-[3-(4-fluorophenoxy)propyl]-3-methoxy-4-piperidinyl}-2-methoxybenzamide (2 g, 4.3 mmoles) [prepared according to the procedure described in Published European Patent Application No. 76,530 (1983)]. The product was crystallized from 2-propanol to give the title product in 54% yield, mp. 146°–148° C.

Anal. Calc'd. for $C_{22}H_{27}ClFN_3O_4$: C, 58.34; H, 6.01; N, 9.28; Cl, 7.83 Found: C, 58.31; H, 6.19; N, 9.12; Cl, 7.88.

(B)

Cis-4-amino-5-chloro-N-{1-[3-(4-fluorophenoxy)-propyl]-3-methoxy-4-piperidinyl}-2-[2-(methylthio)ethoxy]benzamide monohydrate The product from Step A (0.45 g, 1 mmole) was added to a stirred suspension of sodium hydride (40 mg, 1 mmole of 60%, washed with petroleum ether) in acetonitrile (10 ml) followed by tetrabutylammonium bromide (0.32 g, 1 mmole). The reaction mixture was heated to 40° C. for 15 minutes, and there was then added 2-chloro-ethyl methyl sulfide (0.44 g, 4 mmole) and potassium iodide (50 mg). The mixture was heated to reflux for 2 hours. The solvent was evaporated and the residue was partitioned between ethyl acetate (containing 10% of methylene chloride) and water. The organic layer was dried and the solvent evaporated to leave a residue. The residue was crystallized from 2-propanol to yield 0.26 g (50%) of the title compound, mp. 58°–60° C.

Anal. Calc'd. for $C_{25}H_{33}ClFN_3O_4S\cdot H_2O$: C, 55.18; H, 6.48; N, 7.72. Found: C, 55.46; H, 6.42; N, 7.47.

EXAMPLE 62

Cis-4-amino-2-(2-amino-2-oxoethoxy)-5-chloro-N-{1-[3-(4-fluorophenoxy)propyl]-3-methoxy-4-piperidinyl} benzamide sesquihydrate Cis-4-amino-5-chloro-N-{1-[3-(4-fluorophenoxy)-propyl]3-methoxy-4-piperidinyl}-2-hydroxybenzamide (1.35 g, 3 mmoles) (prepared in Example 61, Step A) was added to a stirred suspension of sodium hydride (0.12 g, 3 mmoles of 60% emulsion, washed with petroleum ether) in acetonitrile (20 ml) followed by tetrabutylammonium bromide (0.96 g, 3 mmoles). The reaction mixture was heated to 40° C. for 15 minutes and then treated with methyl bromoacetate (0.92 g, 6 mmoles). After stirring for 2 days the reaction mixture was partitioned between water and ethyl acetate. The organic phase was dried, concentrated in vacuo and the residue was chromatographed over deactivated silica using a methylene chloride (100), methanol (2), ammonia (0.5) solvent system. The appropriate fractions were combined and the solvent evaporated. The residue was dissolved in methylene chloride by adding methanol and the solution was saturated with gaseous ammonia in the cold. After 30 minutes the solvent was evaporated and the residue crystallized from ethanol-water to yield 0.3 g of the title compound as a sesquihydrate (19%), mp. 173°–175° C.

Anal. Calc'd. for $C_{24}H_{30}ClFN_4O_5\cdot 1\frac{1}{2}H_2O$: C, 53.78; H, 6.20; N, 10.45. Found: C, 53.59; H, 6.21; N, 10.36.

The above product was also prepared in the following alternative manner.

Cis-4-amino-5-chloro-N-{1-[3-(4-fluorophenoxy)-propyl]-3-methoxy-4-piperidinyl}-2-hydroxybenzamide (0.68 g, 1.5 mmoles) (prepared in Example 61, Step A) was added to a stirred suspension of sodium hydride (60 mg, 1.5 mmole of 60% emulsion, washed with petroleum ether) in acetonitrile (10 ml) followed by tetrabutylammonium bromide (0.48 g, 1.5 mmole). The reaction mixture was heated to 40° C. for 15 minutes to obtain a clear solution and treated with chloroacetamide (0.56 g, 6 mmoles) potassium iodide (0.25 g) and heated to reflux. The solvent was evaporated and the residue was partitioned between ethyl acetate and water. The residue from the organic layer was chromatographed over deactivated silica using methylene chloride (100), methanol (2), ammonia (0.5) solvent system. The appropriate fractions were combined and the residue (0.2 g) was crystallized from ethanol-water to yield the title compound (60 mg), mp. 173°–175° C.

EXAMPLE 63

4-Amino-5-chloro-N-[(2-diethylamino)ethyl]-2-(2-methoxypropan-1-yloxybenzamide

The general procedure of Example 31 was repeated, except that the 3-bromo-3-methyl-2-butanone used therein was replaced by an equimolar amount of 1-chloro-2-methoxypropane, and the title compound was obtained. Purity, after rechromatography, was >95% (HPLC).

Anal. Calc'd. for $C_{17}H_{28}ClN_3O_3$: C, 57.05; H, 7.89; N, 11.74; Cl, 9.91 Found: C, 56.85; H, 7.92; N, 11.56; Cl, 9.90.

EXAMPLE 64

4-Amino-5-chloro-N-[(2-diethylamino)ethyl]-2-[(2-hydroxy-2-methyl)propan-1-yl]oxybenzamide The general procedure of Example 31 was repeated, except that the 3-bromo-3-methyl-2butanone used therein was replaced by an equimolar amount of 1-chloro-2,3-epoxy-2-methylpropane, and the thus obtained intermediate was reduced with sodium borohydride by the procedure described in Example 41, and the title compound was thereby produced. Mp. 87°–89° C.

EXAMPLE 65

The general procedure of Example 64 is repeated, except that the 1-chloro-2,3-epoxy-2-methylpropane utilized therein is replaced by an equimolar amount of 2-chloro-3,4-epoxy-3-methylbutane, and 4-amino-5-chloro-N-[(2-diethylamino)ethyl]-2-[(2-hydroxy-2-methyl)but-3-yloxybenzamide is thereby produced.

EXAMPLE 66

The general procedure of Example 63 is repeated, except that the 1-chloro-2-methoxypropane utilized therein is replaced by an equimolar amount of 2-chloro-3-methoxybutane, and 2-chloro-3-methoxy-3-methylbutane, respectively, and there is thereby produced
a mixture of threo- and erythro-4-amino-5-chloro-N-[(2-diethylaxino)ethyl]-2-[(2-methoxy)but-3-yl]oxybenzamide, and
4-amino-5-chloro-N-[(2-diethylamino)ethyl]-2-[(2-methoxy-2-methyl)but-3-yl]oxybenzamide, respectively.

We claim:

1. A compound of Formula I having the formula

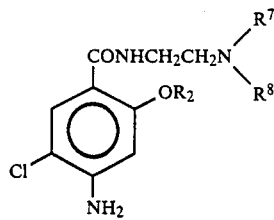

wherein
R$^7$ and R$^8$ are the same or different and are (lower) alkyl;
R$^2$ is

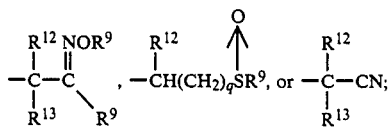

q is an integer of from 0 to 4;
R$^9$ is hydrogen or (lower) alkyl;
R$^{12}$ and R$^{13}$ are the same or different, and are hydrogen, (lower)alkyl, (lower)alknyl, (lower)alkoxy (lower)alkyl or cycloalkyl containing from 5 to 7 carbon atoms inclusive;

or a nontoxic pharmaceutically acceptable salt, hydrate, solvate or quaternary ammonium salt thereof.

2. A compound of claim 1 wherein
R$^7$ and R$^8$ are the same of different and are ethyl or methyl;
R$^2$ is

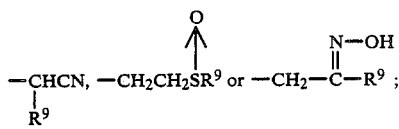

R$^9$ is hydrogen or (lower) alkyl;
or a nontoxic pharmaceutically acceptable salt, hydrate, solvate or quaternary ammonium salt thereof.

3. The compound of claim 2 which is 4-amino-5-chloro-N-[2-diethylamino)ethyl]-2-[(2-hydroxyimino)-propan-1-yl]oxybenzamide, or a nontoixc pharmaceutically acceptable salt, hydrate, ester or quaternary ammonium salt thereof.

4. The compound of claim 1 which is 4-amino-5-chloro-2- cyanomethyloxy-N-[2-(diethylamino)ethyl]-benzamide, or a nontoxic pharmaceutically acceptable salt, hyrdate ester or quaternary ammonium salt thereof.

5. The compound of claim 2 which is 4-amino-5-chloro-N-[2-(diethylamino)ethyl]-2-[2-(methylsulfinyl-)ethoxy]benzamide, or a nontoxic pharmaceutically acceptable salt, hydrate, ester or quaternary ammonium salt thereof.

6. A pharmaceutical composition for the alleviation of nausea and vomiting, which comrises an effective antiemetic amount of at least one compound of claim 1, or a salt, hydrate or solvate thereof, plus a pharmaceutically acceptable carrier.

7. A pharmaceutical composition for the treatment of disorders related to impaired gastric motility, which comprises an effective gastric motility facilitating amount of at least one compound of claim 1, or a salt, hydrate or solvate thereof, and a pharmaceutically acceptable carrier.

8. A method of alleviating nausea and vomiting in a warm-blooded mammal in need thereof, which comprises administering to said mammal an effective antiemetic amount of at least one compound of claim 1, or a salt, hydrate or solvate thereof, in a pharmaceutically acceptable carrier.

9. A method of treating disorders related to impaired gastric motility in a warm-blooded mammal, which comprises administering to said mammal an effective gastric motility facilitating amount of at least one compound of claim 1, or a salt, hydrate or solvate thereof, in a pharmaceutically acceptable carrier.

* * * * *